(12) United States Patent
Speronello et al.

(10) Patent No.: US 8,518,456 B2
(45) Date of Patent: *Aug. 27, 2013

(54) NON-CYTOTOXIC CHLORINE DIOXIDE FLUIDS

(75) Inventors: Barry Keven Speronello, Belle Mead, NJ (US); Frank S. Castellana, Princeton, NJ (US); Linda Hratko, Colonia, NJ (US)

(73) Assignee: BASF Corporation, Florham Park, NJ (US)

( * ) Notice: Subject to any disclaimer, the term of this patent is extended or adjusted under 35 U.S.C. 154(b) by 230 days.

This patent is subject to a terminal disclaimer.

(21) Appl. No.: 12/502,326

(22) Filed: Jul. 14, 2009

(65) Prior Publication Data

US 2010/0062076 A1    Mar. 11, 2010

Related U.S. Application Data

(60) Provisional application No. 61/135,011, filed on Jul. 15, 2008, provisional application No. 61/106,026, filed on Oct. 16, 2008, provisional application No. 61/150,685, filed on Feb. 6, 2009.

(51) Int. Cl.
*A01N 59/00* (2006.01)
*A01N 59/16* (2006.01)
*A01P 1/00* (2006.01)

(52) U.S. Cl.
USPC ............ 424/661; 424/613; 424/615; 424/662

(58) Field of Classification Search
USPC ........................ 424/149, 290, 661; 260/430
See application file for complete search history.

(56) References Cited

U.S. PATENT DOCUMENTS

| | | |
|---|---|---|
| 2,071,091 A | 2/1937 | Taylor |
| 2,701,781 A | 2/1955 | De Guevara |
| 3,123,521 A | 3/1964 | Wentworth et al. |
| 4,060,600 A | 11/1977 | Vit |
| 4,104,190 A | 8/1978 | Hartshorn |
| 4,177,199 A * | 12/1979 | Granatek et al. ............... 556/19 |
| 4,330,531 A | 5/1982 | Alliger |
| 4,585,482 A | 4/1986 | Tice |
| 4,683,039 A | 7/1987 | Twardowski |
| 4,689,215 A | 8/1987 | Ratcliff |
| 4,696,811 A | 9/1987 | Ratcliff |
| 4,786,492 A | 11/1988 | Ratcliff |
| 4,788,053 A | 11/1988 | Ratcliff |
| 4,792,442 A | 12/1988 | Ratcliff |
| 4,793,989 A | 12/1988 | Ratcliff |
| 4,808,389 A | 2/1989 | Ratcliff |
| 4,818,519 A | 4/1989 | Ratcliff |
| 4,837,009 A | 6/1989 | Ratcliff |
| 4,851,213 A | 7/1989 | Ratcliff |
| 4,855,135 A | 8/1989 | Ratcliff |
| 4,886,657 A | 12/1989 | Ratcliff |
| 4,889,714 A | 12/1989 | Ratcliff |
| 4,925,656 A | 5/1990 | Ratcliff |
| 4,975,285 A | 12/1990 | Ratcliff |
| 5,200,171 A | 4/1993 | Ratcliff |
| 5,227,168 A | 7/1993 | Chvapil |
| 5,281,412 A | 1/1994 | Lukacovic |
| 5,348,734 A | 9/1994 | Ratcliff |
| 5,384,134 A | 1/1995 | Kross et al. |
| 5,399,288 A | 3/1995 | Marzouk |
| 5,407,656 A | 4/1995 | Roozdar |
| 5,489,435 A | 2/1996 | Ratcliff |
| 5,597,561 A | 1/1997 | Kross |
| 5,618,550 A | 4/1997 | Ratcliff |
| 5,651,996 A | 7/1997 | Roozdar |
| 5,719,100 A | 2/1998 | Zahradnik |
| 5,820,822 A | 10/1998 | Kross |
| 5,879,691 A | 3/1999 | Sagel |
| 5,944,528 A | 8/1999 | Montgomery |
| 6,007,735 A | 12/1999 | Creed |
| 6,039,934 A | 3/2000 | Alliger |
| 6,046,243 A | 4/2000 | Wellinghoff |
| 6,077,495 A | 6/2000 | Speronello |
| 6,077,502 A | 6/2000 | Witt |
| 6,106,284 A | 8/2000 | Cronin |
| 6,238,643 B1 | 5/2001 | Thangaraj |
| 6,280,775 B1 | 8/2001 | Sasson |
| 6,287,551 B1 | 9/2001 | Ratcliff |
| 6,294,108 B1 | 9/2001 | Speronello |
| 6,294,510 B1 | 9/2001 | Norman |
| 6,312,670 B1 | 11/2001 | Montgomery |
| 6,365,131 B1 | 4/2002 | Doshi |
| 6,379,658 B1 | 4/2002 | Marano |
| 6,425,759 B1 | 7/2002 | Cronin |
| 6,432,322 B1 | 8/2002 | Speronello et al. |
| 6,432,387 B1 | 8/2002 | Laizuka |
| 6,479,037 B1 | 11/2002 | Montgomery |
| 6,500,408 B2 | 12/2002 | Chen |
| 6,551,579 B2 | 4/2003 | Sagel |
| 6,582,682 B2 | 6/2003 | Stier |
| 6,669,931 B2 | 12/2003 | Lynch |

(Continued)

FOREIGN PATENT DOCUMENTS

DE    198 54 349 A1    5/2000
DE    19854349 A1      5/2000

(Continued)

OTHER PUBLICATIONS

Mokhlis, et al., "A Clinical Evaluation of Carbamide Peroxide and Hydrogen Peroxide Whitening Agents During Daytime Use", J Am Dent Assoc 2000; 131;1269-1277.

(Continued)

*Primary Examiner* — Walter Webb

(74) *Attorney, Agent, or Firm* — Elizabeth Pietrowski

(57) ABSTRACT

Disclosed are compositions related to a substantially non-cytotoxic chlorine dioxide solution. The solution may be a thickened fluid composition. Also disclosed are methods of making and using a substantially non-cytotoxic thickened fluid compositions or solutions comprising chlorine dioxide solution. An oxidizing composition of reduced irritation is also disclosed.

15 Claims, No Drawings

(56) References Cited

U.S. PATENT DOCUMENTS

| | | |
|---|---|---|
| 6,682,721 B2 | 1/2004 | Kim |
| 6,699,404 B2 | 3/2004 | Speronello et al. |
| 6,759,030 B2 | 7/2004 | Kosti |
| 6,848,905 B2 | 2/2005 | Jacobs |
| 6,896,518 B2 | 5/2005 | Jacobs |
| 6,964,571 B2 | 11/2005 | Andersen |
| 7,004,756 B2 | 2/2006 | Andersen |
| 7,040,897 B2 | 5/2006 | Fischer |
| 7,087,190 B2 | 8/2006 | Hei |
| 7,087,208 B2 | 8/2006 | Sampson |
| 7,182,883 B2 | 2/2007 | Speronello |
| 7,220,367 B2 | 5/2007 | Speronello |
| 7,229,647 B2 | 6/2007 | Lee et al. |
| 7,273,567 B1 | 9/2007 | Wellinghoff |
| 7,514,019 B2 | 4/2009 | Martin |
| 7,534,368 B2 | 5/2009 | Martin |
| 7,875,460 B2 | 1/2011 | Ratcliff et al. |
| 8,303,939 B2 | 11/2012 | Speronello et al. |
| 8,377,423 B2 | 2/2013 | Speronello et al. |
| 2002/0137728 A1 | 9/2002 | Montgomery |
| 2003/0152528 A1 | 8/2003 | Singh |
| 2003/0228264 A1 | 12/2003 | Perna |
| 2003/0235549 A1 | 12/2003 | Singh |
| 2006/0024369 A1 | 2/2006 | Speronello |
| 2006/0045855 A1 | 3/2006 | Sasson |
| 2006/0088498 A1 | 4/2006 | Martin |
| 2006/0099550 A1 | 5/2006 | Faasse |
| 2006/0169949 A1 | 8/2006 | Speronello et al. |
| 2006/0183080 A1 | 8/2006 | Nosov |
| 2006/0223033 A1 | 10/2006 | McLean |
| 2006/0292090 A1 | 12/2006 | Sharma |
| 2007/0172412 A1 | 7/2007 | Hratko et al. |
| 2007/0202095 A1 | 8/2007 | Speronello |
| 2007/0231277 A1 | 10/2007 | Sharma |
| 2007/0298380 A1 | 12/2007 | Allred |
| 2008/0023668 A1 | 1/2008 | Callerame |
| 2008/0025925 A1 | 1/2008 | Allred |
| 2008/0041400 A1 | 2/2008 | Darnell |
| 2009/0016973 A1 | 1/2009 | Ratcliff |
| 2010/0009009 A1 | 1/2010 | Young et al. |
| 2010/0012891 A1 | 1/2010 | Speronello et al. |
| 2010/0012892 A1 | 1/2010 | Speronello et al. |
| 2010/0015066 A1 | 1/2010 | Speronello et al. |
| 2010/0015067 A1 | 1/2010 | Speronello et al. |
| 2010/0015251 A1 | 1/2010 | Speronello et al. |
| 2010/0074970 A1 | 3/2010 | Ratcliff et al. |
| 2010/0221198 A1 | 9/2010 | Ratcliff et al. |
| 2010/0233101 A1 | 9/2010 | Grootveld et al. |
| 2011/0229422 A1 | 9/2011 | Speronello et al. |
| 2011/0236323 A1 | 9/2011 | Speronello et al. |
| 2011/0318282 A1 | 12/2011 | Ratcliff et al. |

FOREIGN PATENT DOCUMENTS

| | | |
|---|---|---|
| EP | 0371728 A1 | 6/1990 |
| JP | 60-105610 A | 6/1985 |
| WO | 9006126 A1 | 6/1990 |
| WO | WO-98/04235 A1 | 2/1998 |
| WO | WO-2004/028498 A1 | 4/2004 |
| WO | WO-2004/062660 A1 | 7/2004 |
| WO | WO-2005/011582 A2 | 2/2005 |
| WO | WO 2007/062347 A2 | 5/2007 |
| WO | 2007079287 A2 | 7/2007 |
| WO | WO 2007/079287 A2 | 7/2007 |
| WO | WO 2007/131970 A1 | 11/2007 |

OTHER PUBLICATIONS

USPTO Office Action, mailed Dec. 29, 2010, in connection with U.S. Appl. No. 12/502,356, filed Jul. 14, 2009, Assignee BASF Catalysts LLC (now BASF Corporation), first named inventor Barry K. Speronello.

Office action mailed Aug. 10, 2011; U.S. Appl. No. 12/502,356, filed Jul. 14, 2009.

Office Action issued Aug. 10, 2011 in U.S. Appl. No. 12/502,356 to Speronello et al.

Communication dated Jul. 26, 2011 in EP09790352.0, national stage of PCT/US09/50441, filed Jul. 14, 2009.

Office Action dated Sep. 12, 2011 in U.S. Appl. No. 12/502,326.

Office Action dated Mar. 2, 2011 in U.S. Appl. No. 12/502,326.

Office Action dated Jun. 10, 2011 in U.S. Appl. No. 12/502,761.

Office Action dated Dec. 28, 2010 in U.S. Appl. No. 12/502,781.

Office Action dated Aug. 10, 2011 in U.S. Appl. No. 12/502,781.

Office Action dated Apr. 27, 2011 in U.S. Appl. No. 12/502,639.

International Search Report published Mar. 11, 2010 in PCT International Application No. PCT/US2009/050541.

International Preliminary Report on Patentability issued Jan. 18, 2011 in PCT International Application No. PCT/US2009/050541.

International Search Report published Mar. 11, 2010 in PCT International Application No. PCT/US2009/050638.

International Preliminary Report on Patentability issued Jan. 18, 2011 in PCT International Application No. PCT/US2009/050638.

Office Action dated Dec. 20, 2011 in U.S. Appl. No. 12/502,925.

Office Action dated Jun. 10, 2011 in U.S. Appl. No. 12/502,925.

International Search Report published Mar. 11, 2010 in PCT International Application No. PCT/US2009/050629.

Office Action dated Mar. 7, 2011 in U.S. Appl. No. 12/502,664.

Office Action dated Dec. 14, 2011 in U.S. Appl. No. 12/502,895.

Office Action dated Feb. 15, 2012 in U.S. Appl. No. 12/502,907.

Office Action dated Feb. 2, 2012 in U.S. Appl. No. 13/054,493.

Office Action dated Nov. 10, 2011 in U.S. Appl. No. 13/054,494.

Office Action dated Jun. 29, 2011 in U.S. Appl. No. 12/502,895.

Office Action dated Jul. 5, 2011 in U.S. Appl. No. 12/502,907.

United States Environmental Protection Agency correspondence dated Jun. 17, 2010 regarding PUROGENE® product label.

United States Environmental Protection Agency correspondence dated Jun. 18, 1985 regarding ODORID® product label.

Material Safety Data Sheet for "Carnebon® 200 Stabilized chlorine dioxide solution" dated Apr. 5, 2011 (DuPont, Wilmington, DE).

* cited by examiner

NON-CYTOTOXIC CHLORINE DIOXIDE FLUIDS

CROSS-REFERENCE TO RELATED APPLICATIONS

This application claims the benefit pursuant to 35 U.S.C. §119(e) of U.S. Provisional Application Nos. 61/135,011, filed on Jul. 15, 2008; 61/106,026, filed Oct. 16, 2008; and 61/150,685, filed Feb. 6, 2009, each of which is hereby incorporated by reference in its entirety herein.

BACKGROUND

Chlorine dioxide ($ClO_2$) is a neutral compound of chlorine in the +IV oxidation state. It disinfects by oxidation; however, it does not chlorinate. It is a relatively small, volatile, and highly energetic molecule, and a free radical even in dilute aqueous solutions. Chlorine dioxide functions as a highly selective oxidant due to its unique, one-electron transfer mechanism in which it is reduced to chlorite ($ClO_2^-$). The pKa for the chlorite ion/chlorous acid equilibrium, is extremely low (pH 1.8). This is remarkably different from the hypochlorous acid/hypochlorite base ion pair equilibrium found near neutrality, and indicates that the chlorite ion will exist as the dominant species in drinking water.

One of the most important physical properties of chlorine dioxide is its high solubility in water, particularly in chilled water. In contrast to the hydrolysis of chlorine gas in water, chlorine dioxide in water does not hydrolyze to any appreciable extent but remains in solution as a dissolved gas.

The traditional method for preparing chlorine dioxide involves reacting sodium chlorite with gaseous chlorine ($Cl_2$ (g)), hypochlorous acid (HOCl), or hydrochloric acid (HCl). The reactions are:

$$2NaClO_2 + Cl_2(g) \rightarrow 2ClO_2(g) + 2NaCl \quad [1a]$$

$$2NaClO_2 + HOCl \rightarrow 2ClO_2(g) + NaCl + NaOH \quad [1b]$$

$$5NaClO_2 + 4HCl \rightarrow 4ClO_2(g) + 5NaCl + 2H_2O \quad [1c]$$

Reactions [1a] and [1b] proceed at much greater rates in acidic medium, so substantially all traditional chlorine dioxide generation chemistry results in an acidic product solution having a pH below 3.5. Also, because the kinetics of chlorine dioxide formation are high order in chlorite anion concentration, chlorine dioxide generation is generally done at high concentration (>1000 ppm), which must be diluted to the use concentration for application.

Chlorine dioxide may also be prepared from chlorate anion by either acidification or a combination of acidification and reduction. Examples of such reactions include:

$$2NaClO_3 + 4HCl \rightarrow 2ClO_2 + Cl_2 + 2H_2O + 2NaCl \quad [2a]$$

$$2HClO_3 + H_2C_2O_4 \rightarrow 2ClO_2 + 2CO_2 + 2H_2O \quad [2b]$$

$$2NaClO_3 + H_2SO_4 + SO_2 \rightarrow 2ClO_2 + 2NaHSO_4 \quad [2c]$$

At ambient conditions, all reactions require strongly acidic conditions; most commonly in the range of 7-9 N. Heating of the reagents to higher temperature and continuous removal of chlorine dioxide from the product solution can reduce the acidity needed to less than 1 N.

A method of preparing chlorine dioxide in situ uses a solution referred to as "stabilized chlorine dioxide." Stabilized chlorine dioxide solutions contain little or no chlorine dioxide, but rather, consists substantially of sodium chlorite at neutral or slightly alkaline pH. Addition of an acid to the sodium chlorite solution activates the sodium chlorite, and chlorine dioxide is generated in situ in the solution. The resulting solution is acidic. Typically, the extent of sodium chlorite conversion to chlorine dioxide is low and a substantial quantity of sodium chlorite remains in the solution.

WO 2007/079287 teaches that the contamination of chlorine dioxide solutions with alkali metal salts accelerates decomposition of aqueous chlorine dioxide solutions. WO 2007/079287 further discloses a method of preparing a storage-stable aqueous chlorine dioxide solution, wherein the solution contains about 2500 ppm or less of alkali metal salt impurities. Alkali metal salt impurities disclosed are sodium chloride, magesium chloride, calcium chloride and sodium sulfate.

Chlorine dioxide is known to be a disinfectant, as well as a strong oxidizing agent. The bactericidal, algaecidal, fungicidal, bleaching, and deodorizing properties of chlorine dioxide are also well known. Therapeutic and cosmetic applications for chlorine dioxide are known.

For example, U.S. Pat. No. 6,287,551 discusses the use of chlorine dioxide solutions for the treatment of Herpes virus infection. U.S. Pat. No. 5,281,412 describes chlorite and chlorine dioxide compositions that provide antiplaque and antigingivitis benefits without staining the teeth.

U.S. Pat. No. 6,479,037 discloses preparing a chlorine dioxide composition for tooth whitening wherein the composition is prepared by combining a chlorine dioxide precursor (CDP) portion with an acidulant (ACD) portion. The CDP portion is a solution of metal chlorite at a pH greater than 7. The ACD is acidic, preferably having a pH of 3.0 to 4.5. The CDP is applied to the tooth surface. The ACD is then applied over the CDP to activate the metal chlorite and produce chlorine dioxide. The pH at the contact interface is preferably less than 6 and, most preferably, in the range of about 3.0 to 4.5. Thus, the resulting chlorine dioxide composition on the tooth surface is acidic. Additionally, this method exposes the oral mucosa to possible contact with a highly acidic reagent (ACD).

However, all of the above patents describe the use of compositions and methods that are damaging to biological tissues, including soft tissues and hard tissues, such as tooth enamel and dentin. Furthermore, despite being effective for many different purposes, the unthickened, runny, and liquid consistency of many of these solutions limits the potential uses of the solution and often requires concerted effort from a user to ensure the solution is being applied in an effective manner.

What is needed are compositions and methods for the use of chlorine dioxide, wherein biological tissue is not damaged. Additionally, a thickened chlorine dioxide mixture is needed that has the consistency needed to remain on a surface or substrate for any period of time and the chlorine dioxide concentration needed to be effective thereon without requiring significant concerted effort from the user. The present disclosure meets and addresses these needs.

SUMMARY

The following summary is not an extensive overview. It is intended to neither identify key or critical elements of the various embodiments, not delineate the scope of them.

In one aspect, a thickened fluid composition is provided. The thickened fluid composition comprises chlorine dioxide; a thickener component; and an aqueous fluid, and is substantially non-cytotoxic. In an embodiment, the thickened fluid composition comprises less than about 0.2 milligrams oxychlorine anion per gram composition. In an embodiment, the thickened fluid composition comprises about 5 to about 2000 ppm chlorine dioxide. In an embodiment, the thickened fluid composition has a pH from about 4.5 to about 11. In some embodiments of the thickened fluid, the thickener component is selected from the group consisting of natural hydrocolloids, semisynthetic hydrocolloids, synthetic hydrocolloids, and clay. In an embodiment, the thickener component is a semisynthetic hydrocolloid. An exemplary semisynthetic hydrocolloid is carboxymethylcellulose, such as sodium carboxymethylcellulose.

The thickened fluid composition can comprise one or more components selected from an antibacterial agent and a malodor controlling agent. In an embodiment, the antibacterial agent is one of silver and a quaternary ammonium compound.

In one aspect, a fluid composition is provided. The fluid composition comprises chlorine dioxide and an aqueous fluid, and is substantially non-cytotoxic. In an embodiment, the fluid composition comprises less than about 0.2 milligrams oxy-chlorine anion per gram composition. In an embodiment, the fluid composition comprises about 5 to about 2000 ppm chlorine dioxide. In an embodiment, the fluid composition has a pH from about 4.5 to about 11.

In another aspect, a composition for generating a thickened fluid comprising substantially pure chlorine dioxide is provided. The composition comprises a mixture of particulate chlorine-dioxide-forming reactants and a thickener component, wherein the chlorine-dioxide-forming reactants comprise a metal chlorite, an acid source, and an optional halogen source, and the mixture is treated with a stabilizing component. In one embodiment, the composition further comprises an aqueous fluid. In an embodiment, the mixture can be activated for reaction with the aqueous fluid by breaking, heating or exposing to electromagnetic energy the stabilizing component.

Also provided is a method of making a substantially non-cytotoxic thickened fluid composition comprising chlorine dioxide. The method comprises the step of combining a substantially pure chlorine dioxide solution with a thickener component to form a substantially non-cytotoxic thickened fluid composition. In an embodiment, the method further comprises the step of preparing the substantially pure chlorine dioxide solution. The step of preparing the substantially pure chlorine dioxide solution can comprise dissolving a solid body in water, wherein the solid body comprises a metal chlorite, an acid source and a optional source of free halogen. Optionally, the metal chlorite is sodium chlorite, the acid source comprises sodium bisulfate and/or the source of free halogen comprises a material selected from the group consisting of dichloroisocyanuric acid, a salt of dichloroisocyanuric acid, a hydrated salt of dichloroisocyanuric acid and combinations thereof. Optionally, the solid body further comprises one or both of magnesium chloride and sodium chloride. In an embodiment, the substantially non-cytotoxic thickened fluid composition comprises less than about 0.2 milligrams oxy-chlorine anion per gram composition. In an embodiment, the substantially non-cytotoxic thickened fluid composition comprises about 5 to about 2000 ppm chlorine dioxide. In an embodiment, the substantially non-cytotoxic thickened fluid composition has a pH from about 4.5 to about 11. In some embodiments, the thickener component is selected from the group consisting of natural hydrocolloids, semisynthetic hydrocolloids, synthetic hydrocolloids, and clay. In an embodiment, the thickener component is a semisynthetic hydrocolloid. An exemplary semisynthetic hydrocolloid is carboxymethylcellulose, such as sodium carboxymethyl cellulose.

DETAILED DESCRIPTION

The following description sets forth in detail certain illustrative aspects and implementations of the embodiments. These are indicative, however, of but a few of the various ways in which the principles of the various compositions and devices may be employed. Other objects, advantages, and novel features of the compositions, devices, systems and methods will become apparent from the following detailed description.

Thickened mixtures of chlorine dioxide are known in the art, as are aqueous solutions of chlorine dioxide. It has been discovered that such chlorine dioxide compositions can be cytotoxic. Previously, the basis of cytotoxicity of such solutions and thickened compositions was unknown. It is shown herein that oxy-chlorine anions present in chlorine dioxide solutions or thickened compositions are cytotoxic to biological tissues and materials. Accordingly, provided are substantially non-cytotoxic compositions comprising chlorine dioxide. In some embodiments, the compositions are thickened compositions. The substantially non-cytotoxic compositions are useful in therapeutic and cosmetic applications.

Also provided are methods of preparing such compositions.

In some embodiments, the thickened mixtures of chlorine dioxide are produced by adding thickener agents such as clays, polymers, gums, etc. to aqueous solutions of substantially pure chlorine dioxide to produce the thickened and pseudoplastic aqueous fluid mixtures. In other embodiments, particulate chlorine-dioxide-forming reactants are mixed with a thickener component in an aqueous medium.

An advantage of substantially non-cytotoxic solutions comprising chlorine dioxide is ease of use with a reduced or eliminated risk of cytotoxic reaction upon contact with biological tissue and material. For instance, use of a noncytotoxic chlorine dioxide solution as a topical disinfectant reduces or eliminates the need for protective gear, such as gloves, shields and gowns, or for extensive removal of residual solution or other clean up after use.

An advantage of a thickened mixture comprising chlorine dioxide is better adherence to non-horizontal or substantially vertical surfaces. In addition, thickened compositions have reduced volatility of chlorine dioxide relative to an unthickened chlorine dioxide solution. The volatility of chlorine dioxide is reduced because the mass transfer of chlorine dioxide from the interior of the thickened mixture to the surface is inhibited.

Definitions

Unless defined otherwise, all technical and scientific terms used herein generally have the same meaning as commonly understood by one of ordinary skill in the art. Generally, the nomenclature used herein and the laboratory procedures in cytopathicity analysis, microbial analysis, organic and inorganic chemistry, and dental clinical research are those well known and commonly employed in the art.

As used herein, each of the following terms has the meaning associated with it in this section.

The articles "a" and "an" are used herein to refer to one or to more than one (i.e., to at least one) of the grammatical object of the article. By way of example, "an element" means one element or more than one element.

The term "about" will be understood by persons of ordinary skill in the art and will vary to some extent on the context in which it is used. Generally, "about" encompasses a range of values that are plus/minus 10% of a reference value. For instance, "about 25%" encompasses values from 22.5% to 27.5%.

It is understood that any and all whole or partial integers between any ranges set forth herein are included herein.

As used herein, "biocidal" refers to the property of inactivating or killing pathogens, such as bacteria, algae and fungi.

As used herein, an "efficacious amount" of an agent is intended to mean any amount of the agent that will result in a desired biocidal effect, a desired cosmetic effect, and/or a desired therapeutic biological effect. In one example, an efficacious amount of an agent used for tooth whitening is an amount that will result in whitening of a tooth with one or more treatments.

The term "performance efficacy" refers to the performance of a composition comprising an oxidizing agent in a particular test intended to duplicate or simulate in-use performance. For example, an in vitro study of bacterial kill may be used to simulate performance of a composition intended for use as a hard surface disinfectant. Similarly, an in vitro study of the degree of bleaching of extracted human teeth may be used to simulate tooth whitening performance of a composition intended for tooth whitening.

As used herein, "biological tissue" refers to an animal tissue including one or more of: mucosal tissue, epidermal tissue, dermal tissue, and subcutaneous tissue (also called hypodermis tissue). Mucosal tissue includes buccal mucosa, other oral cavity mucosa (e.g., soft palate mucosa, floor of mouth mucosa and mucosa under the tongue), vaginal mucosa and anal mucosa. These mucosal tissues are collectively referred to herein as "soft tissue." Biological tissue may be intact or may have one or more incisions, lacerations or other tissue-penetrating opening. In some embodiments, biological tissue is mammalian tissue.

As used herein, "biological material" includes, but is not limited to, tooth enamel, dentin, fingernails, toe nails, hard keratinized tissues and the like, found in animals, such as mammals.

As used herein, "cytotoxic" refers to the property of causing lethal damage to mammalian cell structure or function. A composition is deemed "substantially non-cytotoxic" or "not substantially cytotoxic" if the composition meets the United States Pharmacopeia (USP) biological reactivity limits of the Agar Diffusion Test of USP<87> "Biological Reactivity, in vitro," (approved protocol current in 2007) when the active pharmaceutical ingredient (API) is present in an efficacious amount.

As used herein, "irritating" refers to the property of causing a local inflammatory response, such as reddening, swelling, itching, burning, or blistering, by immediate, prolonged, or repeated contact. For example, inflammation of the gingival tissue in a mammal is an indication of irritation to that tissue. A composition is deemed "substantially non-irritating" or "not substantially irritating" if the composition is judged to be slightly or not irritating using any standard method for assessing dermal or mucosal irritation. Non-limiting examples of methods useful for assessing dermal irritation include the use of in vitro tests using tissue-engineered dermal tissue, such as EpiDerm™ (MatTek Corp., Ashland, Mass.), which is a human skin tissue model (see, for instance, Chatterjee et al., 2006, Toxicol Letters 167: 85-94) or ex vivo dermis samples. Non-limiting examples of methods useful for mucosal irritation include: HET-CAM (hen's egg test-chorioallantoic membrane); slug mucosal irritation test; and in vitro tests using tissue-engineered oral mucosa or vaginal-ectocervical tissues. Other useful method of irritation measurement include in vivo methods, such as dermal irritation of rat or rabbit skin. See, for instance, the Draize skin test (OECD, 2002, Test Guidelines 404, Acute Dermal Irritation/Corrosion) and EPA Health Effects Testing Guidelines; OPPTS 870.2500 Acute Dermal Irritation. The skilled artisan is familiar with art-recognized methods of assessing dermal or mucosal irritation.

As used herein, "oxy-chlorine anion" refers to chlorite ($ClO_2^-$) and/or chlorate ($ClO_3^-$) anions.

As used herein, "substantially pure chlorine dioxide solution" refers to a solution of chlorine dioxide that has a non-cytotoxic concentration of oxy-chlorine anion. As used herein, "substantially pure chlorine dioxide solution" also refers to a concentrated solution of chlorine dioxide that contains a concentration of oxy-chlorine anion that, upon dilution to an efficacious amount of chlorine dioxide, is not cytotoxic with respect to the concentration of oxy-chlorine anion.

The term "stable," as used herein, is intended to mean that the components used to form chlorine dioxide, i.e., the chlorine dioxide forming ingredients, are not immediately reactive with each other to form chlorine dioxide. It will be understood that the components may be combined in any fashion, such as sequentially and/or simultaneously, so long as the combination is stable until such time that $ClO_2$ is to be generated.

The term "non-reactive," as use herein, is intended to mean that a component or ingredient as used is not immediately reactive to an unacceptable degree with other components or ingredients present to form chlorine dioxide or mitigate the ability of any component or ingredient to perform its function in the formulation at the necessary time. As the skilled artisan will recognize, the acceptable timeframe for non-reactivity will depend upon a number of factors, including how the formulation is to be formulated and stored, how long it is to be stored, and how the formulation is to be used. Accordingly, the timeframe for "not immediately reactive" will range from one or more minutes to one or more hours to one or more weeks. In one embodiment, the timeframe is a range of minutes, for instance, from one minute to about 60 minutes. In another embodiment, the timeframe is a range of hours, for instance, from about one hour to about 24 hours. In yet another embodiment, the timeframe is a range of days, for instance, from about one day to about one week. In yet another embodiment, the timeframe is a range of weeks, for instance, from about one week to about 4-6 weeks.

The phrase "thickened fluid composition" encompasses compositions which can flow under applied shear stress and which have an apparent viscosity when flowing that is greater than the viscosity of the corresponding aqueous chlorine dioxide solution of the same concentration. This encompasses the full spectrum of thickened fluid compositions, including: fluids that exhibit Newtonian flow (where the ratio of shear rate to shear stress is constant and independent of shear stress), thixotropic fluids (which require a minimum yield stress to be overcome prior to flow, and which also exhibit shear thinning with sustained shear), pseudoplastic and plastic fluids (which require a minimum yield stress to be overcome prior to flow), dilantant fluid compositions (which increase in apparent viscosity with increasing shear rate) and other materials which can flow under applied yield stress.

A "thickener component," as the phrase is used herein, refers to a component that has the property of thickening a solution or mixture to which it is added. A "thickener component" is used to make a "thickened fluid composition" as described above.

The phrase "apparent viscosity" is defined as the ratio of shear stress to shear rate at any set of shear conditions which result in flow. Apparent viscosity is independent of shear stress for Newtonian fluids and varies with shear rate for non-Newtonian fluid compositions.

The term "hydrophobic" or "water-insoluble" as employed herein with respect to organic polymers refers to an organic polymer that has a water solubility of less than about one gram per 100 grams of water at 25° C.

As used herein the term "acid source" refers to a material, usually a particulate solid material, which is itself acidic or produces an acidic environment when in contact with liquid water or solid oxy-chlorine anion.

The term "particulate" is defined to mean all solid materials. By way of a non-limiting example, particulates may be interspersed with each other to contact one another in some way. These solid materials include particles comprising big particles, small particles or a combination of both big and small particles.

As used herein, the term "source of free halogen" or "free halogen source" means a compound or mixtures of compounds which release halogen upon reaction with water.

As used herein, the term "free halogen" means halogen as released by a free halogen source.

As used herein, a "particulate precursor of chlorine dioxide" refers to a mixture of chlorine-dioxide-forming reactants that are particulate. Granules of ASEPTROL (BASF, Florham Park, N.J.) are an exemplary particulate precursor of chlorine dioxide.

As used herein, the term "solid body" means a solid shape, typically a porous solid shape, or a tablet comprising a mixture of granular particulate ingredients wherein the size of the particulate ingredients is substantially smaller than the size of the solid body.

As used herein, the phrase "oxidizing agent" refers to any material that attracts electrons, thereby oxidizing another atom or molecule and thereby undergoing reduction. Exemplary oxidizing agents include chlorine dioxide and peroxides, such as hydrogen peroxide.

Description

Provided are compositions comprising an oxidizing agent, wherein the agent comprises chlorine dioxide, which compositions are substantially non-cytotoxic. In some embodiments, the composition comprises a single oxidizing agent, wherein the agent is chlorine dioxide. In some embodiments, the compositions are also substantially non-irritating. The present compositions depart from the chlorine dioxide forms of the prior art, which may contain cytotoxic levels of oxy-chlorine anions and which may also be unthickened and runny.

In one aspect, the prior art compositions of chlorine dioxide have limited applications due to the consistency and concentration of the chlorine dioxide solutions. The consistency of the prior art forms of chlorine dioxide often requires a user to make a concerted effort to ensure that the particular type of chlorine dioxide form is maintained on an intended surface. The thickened chlorine dioxide composition, on the other hand, provides better adherence to many substrates and surfaces than unthickened chlorine dioxide solutions. Substantially non-horizontal surfaces, including vertical surfaces, are better served by the thickened chlorine dioxide whether used alone or with a chlorine dioxide support device. The thickened chlorine dioxide compositions can exhibit reduced volatility of chlorine dioxide relative to unthickened chlorine dioxide solutions.

Prior art forms of chlorine dioxide solutions and compositions have limited biological applications due to oxy-chlorine anions and highly acidic pH. Typical chlorine dioxide solutions include significant levels of oxy-chlorine anions (chlorite ($ClO_2^-$) and/or chlorate ($ClO_3^-$)). As demonstrated herein, it is predominantly the oxy-chlorine anions, and not, for instance, free chlorine, found in chlorine dioxide solutions known in the prior art, that renders the prior art solutions cytotoxic to biological tissues and materials.

Further provided is an oxidizing composition comprising chlorine dioxide as a first oxidizing agent and at least one second oxidizing agent, such as a peroxide-based agent. The oxidizing composition is associated with a reduced irritation relative to a reference oxidizing composition of comparable performance efficacy but without the chlorine dioxide. Methods of their preparation are also provided.

The various aspects of the present compositions, as set forth herein, overcome the limitations of the prior art. In an embodiment, aqueous solutions and thickened fluid compositions of chlorine dioxide are provided, wherein the solutions and compositions are substantially non-cytotoxic. In yet another embodiment, chlorine dioxide-forming compositions are provided, which may be used to prepare non-cytotoxic chlorine dioxide-containing compositions, as described herein. In yet another embodiment, oxidizing compositions of reduced cytotoxicity are provided. Methods for the preparation and use of the substantially non-cytotoxic chlorine dioxide solutions and thickened fluid compositions are also set forth herein.

Composition

The substantially non-cytotoxic composition is an aqueous fluid that comprises chlorine dioxide, or the reactants for generating chlorine dioxide (e.g., chlorine-dioxide-forming reactants). In some embodiments, the composition further comprises a thickener component which renders the composition a thickened aqueous fluid. In another embodiment, the composition is an unthickened solution. Further provided is a precursor composition useful for preparing a substantially non-cytotoxic chlorine dioxide composition. In some embodiments, the non-cytotoxic composition may comprise a non-cytotoxic amount of a second oxidizing component. In one embodiment, the second oxidizing component is a peroxide component. In other embodiments, the non-cytotoxic composition excludes a second oxidizing component, such as a peroxide component.

The amount of chlorine dioxide in a composition will relate to the intended use of the composition. The skilled artisan can readily determine the appropriate amount or amount range of chlorine dioxide to be efficacious for a given use. Generally, compositions useful in the practice of the method comprise at least about 5 parts-per-million (ppm) chlorine dioxide, at least about 20 ppm, and at least about 30 ppm. Typically, the amount of chlorine dioxide can be up to about 1000 ppm, up to about 700 ppm up to about 500 ppm and up to about 200 ppm. In certain embodiments, the chlorine dioxide concentration ranges from about 5 to about 700 ppm, from about 20 to about 500 ppm, and from about 30 to about 200 ppm chlorine dioxide. In one embodiment, the composition comprises about 30 to about 40 ppm chlorine dioxide. In one embodiment, the composition comprises about 30 ppm chlorine dioxide. In another embodiment, the composition comprises about 40 ppm chlorine dioxide. Lower concentrations in the range of about 5 to about 500 ppm are useful when used in the mouth or near the nose so as to minimize exposure to the chlorine-like odor of a chlorine dioxide-containing composition. Higher concentrations in the range of about 20 to about 2000 ppm are useful when used in areas containing a substantial concentration of reactive organic material, such as wound fluid in wounds. Higher concentrations may also be advantageous to accelerate efficacy when treating relatively inert materials, such as dentures, outside of the oral cavity.

For compositions comprising an oxidizing agent consisting of chlorine dioxide, as shown herein, cytotoxicity results predominantly from the presence of oxy-chlorine anions. Accordingly, a composition comprising chlorine dioxide that comprises zero milligram (mg) oxy-chlorine anion per gram composition to no more than about 0.25 mg oxy-chlorine anion per gram composition, zero to about 0.24, 0.23, 0.22, 0.21, or 0.20 mg oxy-chlorine anion per gram composition, zero to about 0.19, 0.18, 0.17, 0.16, 0.15, 0.14, 0.13, 0.12, 0.11, or 0.10 mg oxy-chlorine anion per gram composition or from zero to about 0.09, 0.08, 0.07, 0.06, 0.05 or 0.04 mg oxy-chlorine anion per gram composition, absent other constituents that contribute to cytotoxicity, is substantially non-cytotoxic.

Soft tissue irritation can result from extremes of pH, both acidic and basic. To minimize soft tissue irritation by the chlorine dioxide containing composition, the substantially non-cytotoxic composition has a pH of at least about 3.5. In some embodiments, the composition has a pH of at least about 5, or greater than about 6. In certain embodiments, the pH ranges from about 4.5 to about 11, from about 5 to about 9, or from greater than about 6 and less than about 8. In one embodiment, the pH is about 6.5 to about 7.5. The concentration of oxy-chlorine anions is not believed to contribute to soft tissue irritation.

A substantially non-cytotoxic composition comprising chlorine dioxide can be prepared using a substantially pure chlorine dioxide solution having a neutral pH. In some embodiments, the substantially pure chlorine dioxide solution has a pH from about 5 to about 9, or, from about 6.5 to about 7.5.

Substantially pure chlorine dioxide may be prepared by any known method, then bubbling a gas (e.g., air) through that solution (sparging) and into a second container of deionized water, to prepare the product solution of substantially pure chlorine dioxide. Only $ClO_2$ and possibly some water vapor is transferred from the source solution to the product solution. All the salt ingredients and acid remain behind in the source solution. Thus, there are no oxy-chlorine anions in the substantially pure product solution. One method of preparing chlorine dioxide comprises combining an aqueous solution of sodium chlorite with a mineral acid to reduce the solution pH to below about 3.5 and allowing the solution to react for a sufficient time, e.g., about 30 minutes, to generate chlorine dioxide. The resulting solution is then sparged as described above to prepare the product solution of substantially pure chlorine dioxide.

While the substantially pure chlorine dioxide may undergo a degree of decomposition, the rate is relatively slow. By keeping the solution capped and protected from ultraviolet exposure, the decomposition rate can be slowed to a rate of about 5% to about 25% reduction in chlorine dioxide in 7 days. Substantially pure chlorine dioxide may also be prepared using a pervaporation technique, such as that disclosed in U.S. Pat. No. 4,683,039. In addition, a metal chlorite and an acid source can be reacted in solution to yield high conversion to chlorine dioxide and produce a greater than 2000 ppm chlorine dioxide solution. The concentrated solution can then be buffered to a neutral pH. Similarly, a chlorine dioxide solution can be prepared using the composition described in U.S. Pat. No. 5,399,288, which yields a high concentration chlorine dioxide solution at acidic pH. The concentrated solution can then be buffered to achieve a substantially neutral pH to prepare a substantially pure chlorine dioxide solution.

Another source of a substantially pure chlorine dioxide solution is chlorine dioxide is prepared using an ASEPTROL (BASF Corp., Florham Park, N.J.) material, which are described in commonly-assigned U.S. Pat. Nos. 6,432,322 and 6,699,404. These patents disclose substantially anhydrous solid bodies comprising particulate reagents for preparing highly-converted solutions of chlorine dioxide when added to water. The particulate reagents in the solid bodies comprise a metal chlorite such as sodium chlorite, an acid source such as sodium bisulfate and optionally a source of free halogen such as the sodium salt of dichloroisocyanuric acid or a hydrate thereof (collectively referred to herein as "NaDCCA"). Chlorine dioxide is generated when an ASEPTROL material is contacted with water or an aqueous medium. ASEPTROL material can be made to have an extremely high conversion rate in an aqueous solution, as described in U.S. Pat. Nos. 6,432,322 and 6,699,404, resulting in high concentrations of chlorine dioxide and low concentrations of oxy-chlorine anion. Thus, ASEPTROL materials provide a way to efficiently generate chlorine dioxide at substantially neutral pH, thus avoiding problems existing with earlier, acidic chlorine dioxide-based products.

Chlorites useful in preparing the composition include metal chlorites. The metal chlorite can generally be any metal chlorite. In some embodiments, metal chlorites are alkali metal chlorites, such as sodium chlorite and potassium chlorite. Alkaline earth metal chlorites can also be employed. Examples of alkaline earth metal chlorites include barium chlorite, calcium chlorite, and magnesium chlorite. In many embodiments, the metal chlorite is sodium chlorite.

The acid source may include inorganic acid salts, salts comprising the anions of strong acids and cations of weak bases, acids that can liberate protons into solution when contacted with water, organic acids, and mixtures thereof. In another aspect, the acid source in particular applications of the composition is a particulate solid material which does not react substantially with the metal chlorite during dry storage, however, does react with the metal chlorite to form chlorine dioxide when in the presence of the aqueous medium. The acid source may be water soluble, substantially insoluble in water, or intermediate between the two. Exemplary acid sources are those which produce a pH of below about 7, and below about 5.

Exemplary substantially water-soluble, acid-source-forming components include, but are not limited to, water-soluble solid acids such as boric acid, citric acid, tartaric acid, water soluble organic acid anhydrides such as maleic anhydride, and water soluble acid salts such as calcium chloride, magnesium chloride, magnesium nitrate, lithium chloride, magnesium sulfate, aluminum sulfate, sodium acid sulfate ($NaHSO_4$), sodium dihydrogen phosphate ($NaH_2PO_4$), potassium acid sulfate ($KHSO_4$), potassium dihydrogen phosphate ($KH_2PO_4$), and mixtures thereof. In some embodiments, the acid-source-forming component is sodium acid sulfate (sodium bisulfate). Additional water-soluble, acid-source-forming components will be known to those skilled in the art.

As used herein, the term "source of free halogen" or "free halogen source" means a compound or mixtures of compounds which release halogen upon reaction with water. As used herein, the term "free halogen" means halogen as released by a free halogen source. In one embodiment, the free halogen source is a free chlorine source, and the free halogen is free chlorine. Suitable examples of free halogen source used in the anhydrous compositions include dichloroisocyanuric acid and salts thereof such as NaDCCA, trichlorocyanuric acid, salts of hypochlorous acid such as sodium, potassium and calcium hypochlorite, bromochlorodimethylhydantoin, dibromodimethylhydantoin and the like. The exemplary source of free halogen is NaDCCA.

Oxy-chlorine anions can be measured in the chlorine dioxide solutions using any method known to those skilled in the art, including ion chromatography following the general procedures of EPA test method 300 (Pfaff, 1993, "Method 300.0 Determination of Inorganic Anions by Ion Chromatography,"

Rev. 2.1, US Environmental Protection Agency) or a titration method based on an amperometric method (Amperometric Method II in Eaton et al, ed., "Standard Methods for the Examination of Water and Wastewater" 19$^{th}$ edition, American Public Health Association, Washington D.C., 1995). Alternatively, oxy-chlorine anions may be measured by a titration technique equivalent to the amperometric method, but which uses the oxidation of iodide to iodine and subsequent titration with sodium thiosulfate to a starch endpoint in place of the amperometric titration; this method is referred to herein as "pH 7 buffered titration." A chlorite analytical standard can be prepared from technical grade solid sodium chlorite, which is generally assumed to comprise about 80% by weight of pure sodium chlorite.

For non-cytotoxic chlorine dioxide solutions, the substantially pure chlorine dioxide solution may be diluted as necessary to reach the desired concentration of chlorine dioxide. The solution may be diluted with substantially pure water or a buffer to adjust the final pH as desired. To prepare a thickened aqueous composition comprising chlorine dioxide that is substantially not cytotoxic and, in some embodiments, non-irritating, the substantially pure chlorine dioxide solution can be combined with a thickener component and an aqueous medium.

The aqueous thickened fluid composition used in practicing the method may comprise any thickener component in an aqueous medium, wherein the thickened fluid composition is non-cytotoxic and, in some embodiments, non-irritating to soft tissues. In addition, in most embodiments, the thickener is not adversely affected by the chlorine dioxide on the time scale of composition preparation and use in treatment. Many thickener agents are known in the art, including, but not limited to carbomers (e.g., CARBOPOL thickeners, Lubrizol Corp., Wickliffe, Ohio), carboxymethylcellulose (CMC), ethylcellulose, hydroxyethylcellulose, hydroxypropyl cellulose, natural smectite clays (e.g., VEEGEM, R.T. Vanderbilt Co., Norwalk, Conn.), synthetic clays (e.g., LAPONITE (Southern Clay Products, Gonzales, Tex.), methylcellulose, superabsorbent polymers such as polyacrylates (e.g., LUQUASORB 1010, BASF, Florham Park, N.J.), poloxamers (PLURONIC, BASF, Florham Park, N.J.), polyvinyl alcohol, sodium alginate, tragacanth, and xanthan gum. Such thickening agents may be categorized into four groups: natural hydrocolloids (also referred to as "gum"), semisynthetic hydrocolloids, synthetic hydrocolloids, and clay. Some examples of natural hydrocolloids include acacia, tragacanth, alginic acid, carrageenan, locust bean gum, guar gum, and gelatin. Non-limiting examples of semisynthetic hydrocolloids include methylcellulose and sodium carboxymethylcellulose. Some examples of synthetic hydrocolloids (also referred to as "polymers" including polymers, cross-linked polymers, and copolymers) include polyacrylates, superabsorbent polymers, high molecular weight polyethylene glycols and polypropylene glycols, polyethylene oxides and CARBOPOL. Non-limiting examples of clay (including swelling clay) include LAPONITE, attapulgite, bentonite and VEEGUM. In some embodiments, the thickener component is a semisynthetic hydrocolloid. In some embodiments, the thickener component is a carboxymethylcellulose (CMC).

CMC is a cellulose derivative with carboxymethyl groups (—$CH_2$—COOH) bound to some of the hydroxyl groups of the glucopyranose monomers that make up the cellulose backbone. It is synthesized by the alkali-catalyzed reaction of cellulose with chloroacetic acid. The polar (organic acid) carboxyl groups render the cellulose soluble and chemically reactive. The functional properties of CMC depend on the degree of substitution of the cellulose structure (i.e., how many of the hydroxyl groups have taken part in the substitution reaction), and chain length of the cellulose backbone structure.

In an aspect, the CMC is a high viscosity sodium carboxymethylcellulose (NaCMC powder). However, it will be understood that any salt and/or derivative of CMC may be used. The skilled artisan will understand, based on the disclosure set forth herein, which salt or derivative of CMC would be most advantageous based on the physical and chemical properties of the desired composition. In an exemplary embodiment, NaCMC is used for therapeutic and cosmetic applications.

CMC is available in a range of viscosity grades and to USP standards. High viscosity CMC, such as type CA194 from Spectrum Chemical Manufacturing Company, has a viscosity of between 1500 and 3000 cps at 25° C. at 1% concentration in water.

In preparing a non-cytotoxic composition, one or more components of the composition may be combined prior to the time of preparation of the composition. Alternatively, all components of a composition may be prepared at the time of use. For either non-cytotoxic solutions or non-cytotoxic thickened compositions, optional other components suitable for the intended use of the non-cytotoxic chlorine dioxide solution, as described elsewhere herein, may be included. Chlorine dioxide in solution will decompose over time. To avoid problems arising from such decomposition, including loss of efficacy and generation of chlorite anions, the substantially pure chlorine dioxide solution is generally prepared immediately before its dilution or its combination with a thickener component and an aqueous medium. Alternatively, the storage-stable chlorine dioxide solution of WO 2007/079287 can be used, provided the oxy-chlorine anion concentration is sufficiently low to be deemed a substantially pure chlorine dioxide solution.

In addition, the thickened composition comprising chlorine dioxide is generally prepared immediately before its use in a therapeutic or cosmetic application. "Immediately before" as used herein refers to a period no greater than that which would result in diminished efficacy or evidence of cytotoxicity. Generally, "immediately before" is less than about 14 days, no greater than about 24 hours or no greater than about 2 hours. In some embodiments, the substantially pure chlorine dioxide solution is prepared within about 8 hours of the preparation of the composition. Precautions are also taken to avoid exposing the chlorine dioxide solution or the prepared composition to strong ultraviolet light or elevated temperature (e.g., temperature greater than ambient temperature, about 25° C.).

Alternatively, the thickened composition comprising chlorine dioxide may be prepared well in advance of its use using the storage-stable chlorine dioxide solution of WO 2007/079287 provided the oxy-chlorine anion concentration is sufficiently low. Generally, "prepared well in advance" is more than about 14 days, or more than about 60 days. In this embodiment, it is necessary that the thickener component is relatively resistant to oxidation by chlorine dioxide so as to limit possible degradation of chlorine dioxide to chlorite anion, and of the thickener and possible consequential reduction of viscosity of the thickened composition during storage.

Methods of preparing thickened compositions comprising chlorine dioxide are also disclosed in commonly-assigned U.S. Pat. Publication Nos. 2006/0169949 and 2007/0172412. In practicing the methods described in these two publications, steps must be taken (as described herein) to control the oxychlorine concentration so as to produce a non-cytotoxic composition.

A substantially non-cytotoxic thickened composition comprising chlorine dioxide may also be prepared using a particulate precursor of $ClO_2$ and an aqueous thickened fluid composition. Thus also provided is a two-component system comprising a first component comprising a particulate precursor of chlorine dioxide and a second component comprising a thickener component in an aqueous medium. Combination of the first and second components yields a non-cytotoxic composition comprising an amount of chlorine dioxide efficacious for a therapeutic or cosmetic application. As described elsewhere herein, chlorine-dioxide-forming reagents include metal chlorites, metal chlorates, an acid source and an optional halogen source. The particulate precursor may comprise one of these or any combination of these. In some embodiments, the particulate precursor is an ASEPTROL product, such as ASEPTROL S-Tab2. ASEPTROL S-Tab2 has the following chemical composition by weight (%): $NaClO_2$ (7%); $NaHSO_4$ (12%); NaDCC (1%); NaCl (40%); $MgCl_2$ (40%). Example 4 of U.S. Pat. No. 6,432,322 describes an exemplary manufacture process of S-Tab2. Granules can be produced, either by comminuting pressed S-Tab2 tablets, or by dry roller compaction of the non-pressed powder of the S-Tab2 components, followed by breakup of the resultant compacted ribbon or briquettes, and then screening to obtain the desired size granule. Upon exposure to water or an aqueous thickened fluid, chlorine dioxide is generated from the ASEPTROL granules. In one embodiment, a substantially non-cytotoxic composition comprising chlorine dioxide is prepared by combining −40 mesh granules with an aqueous thickened fluid. In one embodiment, the thickener component of the thickened fluid is carboxymethylcellulose. The skilled artisan will recognize that chlorine dioxide production in the thickened fluid composition prepared using a particulate precursor of $ClO_2$, while rapid, is not instantaneous. Thus, sufficient time for the generation of chlorine dioxide, and corresponding consumption of chlorite anion, is necessary to obtain a substantially non-cytotoxic thickened fluid composition. The skilled artisan can readily determine what time is sufficient, in view of the teachings in this disclosure and the knowledge of the art.

The pore size and pore volume ranges of ASEPTROL tablets required to facilitate the desired degree of conversion of chlorite anion to chlorine dioxide will depend upon many factors, e.g., the particular combination of reagents in the solid body, the size of the solid body, the shape of the solid body, the temperature of the water, other chemicals dissolved in the water, the desired degree of conversion of chlorite anion to chlorine dioxide, the desired amount of free halogen to be delivered into the solution, etc. Accordingly, it is not believed that there is a single optimum range of pore sizes or pore volumes that will produce an optimum result. It is within the capability of one skilled in the art to vary the pore size and the pore volume of a solid body, such as a tablet or granule thereof, to achieve the desired result in respect to the substantially non-cytotoxic chlorine dioxide solution or thickened composition. In general, high conversion is favored by several factors, including: using the largest size granules practical; reacting the granules to form chlorine dioxide under conditions which minimize dissolution of chlorite anion into the bulk aqueous phase prior to reaction to form chlorine dioxide (e.g., minimize stirring of the composition during chlorine dioxide formation); and forming the granules in a manner, for example, a high compaction pressure, such that the granules have sufficient strength to maintain their granularity during and after mixing.

In some embodiments, the aqueous thickened fluid is prepared sufficiently in advance of combining with the ASEPTROL granules to enable the complete hydration of the thickener component. In one embodiment, the thickened fluid composition is formed by adding high viscosity NaCMC powder to distilled water. The NaCMC is allowed to hydrate for at least 8 hours, and then the mixture is stirred to homogenize it. A substantially non-cytotoxic composition is then prepared by mixing the sized ASEPTROL granules with the NaCMC thickened fluid. Contact with the aqueous medium in the hydrated NaCMC mixture activates the ASEPTROL granules and chlorine dioxide is generated.

Further provided is a precursor composition useful for preparing the substantially non-cytotoxic thickened fluid composition comprising chlorine dioxide. The precursor composition comprises a mixture containing particulate chlorine-dioxide forming ingredients (a metal chlorite, an acid source, and an optional halogen source), a thickener component, and optionally water, wherein the ingredients are combined so as to be non-reactive, thus forming a stable composition. In one aspect, a stable composition is a composition comprising at least one "stabilizing component," for the purpose of preventing the reaction or degradation of one or more active components prior to the intended use of the composition. In one aspect, a stabilizing component delays the reaction of one or more active components upon introduction of the composition to an aqueous medium.

Stabilizing components useful in the composition include, but are not limited to, coatings or encapsulating materials disposed over one or more of the particulate constituent. Such stabilizing components are designed to be slowly, and not immediately, soluble, or substantially insoluble in the absence of activation of the stabilizing component. Exemplary coatings or encapsulating materials include, e.g., oleophilic materials and hydrophobic (water-insoluble) polymeric materials. Other non-limiting examples of encapsulating or coating materials which can function as stabilizing component include conventional edible gums, resins, waxes, and mineral oils. Such stabilizing coating materials prevent immediate reactions between the mixture containing particulate chlorine-dioxide-forming reagents and the aqueous medium. The stabilized components may be activated for immediate reaction by techniques known to those of ordinary skill in the art, such as, but not limited to, breaking the components or removing or disrupting the stabilizing components to expose the component to aqueous medium by, for example, stirring and heating, or exposure to electromagnetic energy, such as ultraviolet light or ultrasound.

Non-limiting examples of suitable water-insoluble polymers useful as a stabilizing component, alone or in combination with one or more other components, include: polyvinyl acetate, polyacrylamide, polyvinyl chloride, polystyrene, polyethylene, polyurethane, and the like. Non-limiting examples of suitable oleophilic coatings or encapsulating materials include paraffin, mineral oil, edible oils such as peanut oil, coconut oil, palm oil, or safflower oil, oleophilic organic esters such as isopropyl silomane myristate or isopropyl palmitate, edible polysiloxanes, and the like. Encapsulating materials containing a mixture of paraffin and waxes are also suitable stabilizing components.

The stabilizing component may stabilize one or more of the components of the mixture. In an embodiment, at least one of the components is aqueous and the remainder of the components are stabilized. To assure non-cytotoxicity in the final composition, the particulate chlorine-dioxide-forming reactants are combined to form a particulate precursor such that upon exposure to an aqueous medium after activation of the stabilizing component, favorable conditions exist for a high conversion rate, thereby consuming substantially all of the sodium chlorite. In particular, the reactants in the particulate precursor should remain locally concentrated and proximal to each other to provide high conversion upon exposure to an aqueous medium. In some embodiments, the particulate precursor is an ASEPTROL material. In one embodiment, the particulate chlorine-dioxide-forming reactants are encapsulated to prevent immediate activation with water or an aqueous medium, such as an aqueous thickened fluid. In another embodiment, the encapsulated particulate reactants are combined with a thickener component to form a precursor composition. Upon addition of water or an aqueous fluid to the precursor composition, the thickener component will thicken the water or aqueous fluid. The stabilized component may be activated before, during or after the addition of water. In yet another embodiment, the encapsulated particulate reactants, such as encapsulated ASEPTROL granules, may be suspended in a hydrated thickened fluid to form a precursor composition. When generation of chlorine dioxide is desired, the encapsulating material is broken or disrupted, allowing contact of the particulate chlorine-dioxide-forming reagents with the hydrated thickened fluid, thereby activating chlorine dioxide production and forming a substantially non-cytotoxic composition.

In another embodiment, the substantially non-cytotoxic thickened fluid composition may also be formed at the site of intended use. For instance, a body fluid, such as saliva, damp skin or mucus of mucosal tissue, may serve as the aqueous medium to activate particulate precursors of chlorine dioxide, such as ASEPTROL granules. In one embodiment, the mixture may be particulates in the form of a powder and mixed in a layer of thickener component thereby forming a thickened matrix. The matrix may be applied directly to a biological tissue, wherein exposure to moisture present in the biological tissue activates production of chlorine dioxide to form a substantially non-cytotoxic composition. Alternatively, the matrix may be moistened immediately prior to use and then applied to a biological tissue. In another embodiment, a carrier, such as a disposable cloth or paper, may be impregnated with the thickened matrix. The impregnated carrier is then applied to a moist hard surface to activate production of a substantially non-cytotoxic chlorine dioxide composition at the site of use. Alternatively, the impregnated carrier is moistened with an aqueous medium immediately prior to use on the hard surface. In another embodiment, a mixture of ASEPTROL granules and a thickener component is formed into a shape, for instance by addition of a malleable wax, and the shape is then applied to teeth. Saliva activates the granules, forming chlorine dioxide and the thickener component hydrates, thereby forming the thickened fluid composition in situ. In another embodiment, a mixture of ASEPTROL granules and a thickener component is placed on a dental strip, a dental film or in a dental tray. A dental strip refers to a substantially planar object made of a plastic backbone that is sufficiently flexible to affix to teeth. A dental film refers to a substantially planar object made of a pliable, conformable material that can be substantially fitted to the surface of teeth. Optionally, the dental strip is dissolvable in an aqueous medium, such as saliva. The strip, film or tray is positioned on teeth, and saliva serves as the aqueous medium as described above to produce the substantially non-cytotoxic thickened fluid composition in situ. Alternatively, the mixture on the strip or tray is contacted with water or aqueous medium prior to positioning on the teeth.

The amount of oxy-chlorine anion can be accurately estimated by measuring the oxy-chlorine anion in the aqueous solution (prior to thickening), and adjusting the final concentration on the basis of weight of the final thickened fluid. The titration method described elsewhere herein is contemplated as useful in assessing both the chlorine dioxide concentration and the oxy-chlorine anion concentration in thickened fluid compositions. It is contemplated that oxy-chlorine anions in a thickened fluid composition can be measured using ion chromatography as described elsewhere herein, provided steps are taken to preclude fouling of the column by the hydrated thickener component. One such step is the use of molecular weight filters to remove the hydrated thickener component, such as hydrated CMC, prior to application to the chromatography column. If necessary, the thickened fluid composition may be diluted with water, prior to analysis, to reduce its viscosity or otherwise allow it to be more readily tested. One of skill in the art can readily determine empirically whether a given formulation has a sufficiently low oxy-chlorine concentration by determining if the formulation is cytotoxic using USP biological reactivity limits of the Agar Diffusion Test of USP<87>.

An oxidizing composition comprising chlorine dioxide and at least one other oxidizing agent, such as a peroxide-based agent, is also provided. Exemplary second bleaching agents include alkali metal percarbonates (such as sodium percarbonate), carbamide peroxide, sodium perborate, potassium persulfate, calcium peroxide, zinc peroxide, magnesium peroxide, hydrogen peroxide complexes (such as a PVP-hydrogen peroxide complex), hydrogen peroxide, free halogen oxidizing agents such as free chlorine or hypochlorite anion, and combinations thereof In some embodiments, the second bleaching agent is a peroxide-based agent. Peroxide-based oxidizing agents can be both irritating and cytotoxic at efficacious oxidizing concentrations. It is contemplated that a substantially non-cytotoxic chlorine dioxide composition combined with another oxidizing agent will yield a potent oxidizing composition that has reduced irritation, and possibly also reduced cytotoxicity relative to a composition comprising a sufficient quantity of the oxidizing agent to have comparable performance efficacy in the absence of chlorine dioxide. Performance efficacy is assessed with respect to the intended end use. For instance, comparable efficacy for tooth whitening refers to comparable tooth whitening achieved under the same treatment conditions (e.g., change in shade value units achieved after two-30 minute treatments). Such an oxidizing composition is also expected to retain potent bactericidal activity. This composition is useful in any application requiring an oxidizing composition and which may benefit from reduced irritation and may tolerate mild cytotoxicity. Optional components are most usefully relatively resistant to oxidation as described elsewhere herein. The oxidizing composition can be prepared by the methods described herein for non-cytotoxic composition, by incorporating at least one other oxidizing agent. The precursor composition useful for preparing the substantially non-cytotoxic thickened fluid composition may also be used to prepare an oxidizing composition by addition of at least one other oxidizing agent to the prepared non-cytotoxic thickened fluid composition. For example, a thickener may be added to an aqueous solution of hydrogen peroxide to form a thickened hydrogen peroxide mixture. That mixture may then be combined with −40 mesh granules of the ASEPTROL S-Tab2 formulation to generate chlorine dioxide and produce a thickened mixture comprising both chlorine dioxide and hydrogen peroxide. Also contemplated is a precursor composition for an oxidixing composition comprising a particulate precursor of chlorine dioxide and a particulate precursor of at least a second bleaching agent. For instance, a mixed agent precursor composition comprising a particulate precursor of chlorine dioxide and one or more of sodium perborate, potassium persulfate, carbamide peroxide, or an alkali metal percarbonate, when contacted with an aqueous fluid, will generate both chlorine dioxide and hydrogen peroxide. The particulate matter is generally anhydrous or otherwise stabilized to preclude or substantially limit premature activation. Methods to stabilize components are discussed, for instance, in commonly-assigned application entitled "Non-Cytotoxic Chlorine Dioxide Fluids" and in U.S. Patent Publication No. 2007/0172412.

In some embodiments, the oxidizing composition of reduced cytotoxicity comprises chlorine dioxide and a peroxide agent. Representative peroxide agents include, but are not limited to, hydrogen peroxide, sodium peroxide, potassium peroxide, ammonium peroxide, calcium peroxide, magnesium peroxide, zinc peroxide, and carbamide peroxide. In some embodiments, the peroxide agent is hydrogen peroxide. The peroxide agent is present in the composition at greater than about 1% (by weight) and less than about 30%, less than about 10%, or equal to or less than about 6%. To minimize irritation due to extreme pH, the oxidizing compositions generally have a pH greater than 3.5, greater than about 5 or, greater than about 6. As described elsewhere herein, in certain embodiments, the pH ranges from about 4.5 to about 11, from about 5 to about 9, or greater than about 6 and less than about 8.

The compositions are aqueous fluids. In some embodiments, the fluid is a thickened aqueous fluid having flow properties suitable for applying the thickened fluid to a substantially non-horizontal surface and leaving the fluid in place without substantial dripping or running for a period of time. The duration of the period depends on the application. Generally, the period of time ranges from at least about 5 seconds, from at least about 10, 20, 30, 45 or 60 seconds, or from at least about 2, 3, 4, 5, 6, 7, 8, 9, 10 or more minutes. Accordingly, a pseudoplastic composition with a sufficient yield point to retain its shape when applied to a substantially non-horizontal surface but low enough to be readily removed, for instance, by wiping or rinsing with water, is advantageous.

The compositions may optionally comprise other components. Such components will be influenced by the intended use of the composition. For instance, compositions intended for oral cosmetic and/or therapeutic applications may comprise components that include, but are not limited to, sweeteners, flavorants, coloring agents and fragrances. Sweeteners include sugar alcohols. Exemplary sugar alcohols include sorbital, xylitol, lactitol, mannitol, maltilol, hydrogenated starch hydrolysate, erythritol, reducing paratinose and mixtures thereof. Flavoring agents include, e.g., natural or synthetic essential oils, as well as various flavoring aldehydes, esters, alcohols, and other materials. Examples of essential oils include oils of spearmint, peppermint, wintergreen, sassafras, clove, sage, eucalyptus, marjoram, cinnamon, lemon, lime, grapefruit, and orange. Coloring agents include a colorant approved for incorporation into a food, drug or cosmetic by a regulatory agency, such as, for example, FD & C or D & C pigments and dyes approved by the FDA for use in the United States. Fragrances include menthol, menthyl acetate, menthyl lactate, camphor, eucalyptus oil, eucalyptol, anethole, eugenol, cassia, oxanone, α-irisone, propenyl guaiethol, thymol, linalool, benzaldehyde, cinnamaldehyde, N-ethyl-p-menthan-3-carboxamine, N,2,3-trimethyl-2-isopropylbutanamide, 3-(1-menthoxy)-propane-1,2-diol, cinnamaldehyde glycerol acetal (CGA), menthone glycerol acetal (MGA) and the like.

Other optional components for a composition intended for oral cosmetic and/or therapeutic use include: antibacterial agents (in addition to chlorine dioxide), enzymes, malodor controlling agents (in addition to chlorine dioxide), cleaning agents, such as phosphates, antigingivitis agents, antiplaque agents, antitartar agents, anticaries agents, such as a source of fluoride ion, antiperiodontitis agents, nutrients, antioxidants, and the like.

Optional components for a composition intended for topical disinfectant of a hard surface include: fragrance; coloring agent; surfactants; effervescing agents; cleaning agents such as sodium lauryl sulfate; and the like. For topical disinfectant of a biological tissue, optional ingredients include: fragrance; coloring agents; local anesthetics such as menthol, chloroform, and benzocaine; emollients or moisturizers; analgesics; cleaning agents such as sodium lauryl sulfate; antibacterial agents (in addition to chlorine dioxide); malodor controlling agents (in addition to chlorine dioxide); bioadhesive polymers, such as polycarbophil, polyvinylprrolidone, or a mixture thereof; and the like. Thus, a composition comprising chlorine dioxide as a first antibacterial agent or malodor controlling agent and at least one second such agent is also provided. Exemplary antibacterial agents for such a composition include, but are not limited to, silver and quaternary ammonium compounds. In other embodiments, a second antibacterial or malodor controlling agent is excluded from the composition.

In most embodiments, all optional components are relatively resistant to oxidation by chlorine dioxide (and any other oxidizing agent present in the composition), since oxidation of composition components by chlorine dioxide will reduce the available chlorine dioxide for oxidation for its intended function. "Relatively resistant" means that in the time scale of preparing and using the chlorine dioxide-containing composition in an application, the function of the optional component is not unacceptably diminished, and the composition retains an acceptable level of efficacy/potency with respect to the chlorine dioxide (and other oxidizing agents if present) and remains substantially non-cytotoxic (or has reduced cytotoxicity for compositions comprising one or more additional oxidizing agents). In some embodiments, the compositions also remain substantially non-irritating.

The compositions may be used in any application that would benefit from the properties of a substantially non-cytotoxic chlorine dioxide composition. Properties of the chlorine dioxide composition include potent biocidal activity, deodorizing activity and bleaching activity. Applications making use of such properties applications include, but are not limited to, oral care, oral mouthwash, tooth whitening, periodontal disease treatment, caries abatement, hand rinse, denture or toothbrush cleaning, hard surface cleansing, vaginal lavage, enema, wound treatment and care, skin treatment, burned skin treatment, skin bleaching, hair bleaching, odor abatement, fungal infections of toenail, nail, and/or skin, Candida skin and mucosa infection treatment and contact lens disinfection.

Notably, as shown herein, substantially non-cytotoxic chlorine dioxide solutions are highly effective against methicillin-resistant *Staphylococcus aureus* (MRSA) and *Pseudomonas aeruginosa* (*P. Aeruginosa*). MRSA is a resistant variation of the common bacterium *Staphylococcus aureus*. It has evolved an ability to survive treatment with beta-lactamase resistant beta-lactam antibiotics, including methicillin, dicloxacillin, nafcillin, and oxacillin. *P. aerugi-*

*nosa* is a Gram-negative bacteria. The typical *Pseudomonas* bacterium in nature might be found in a biofilm, attached to some surface or substrate. *P. aeruginosa* is notorious for its resistance to antibiotics and is, therefore, a particularly dangerous pathogen. The bacterium is naturally resistant to many antibiotics due to the permeability barrier afforded by its Gram-negative outer membrane. The tendency of *P. aeruginosa* to colonize surfaces in a biofilm form also makes the cells resistant to therapeutic concentrations antibiotics.

Both MRSA and *P. aeruginosa* are especially troublesome in hospital-associated (nosocomial) infections. Both are particularly dangerous for patients with weakened immune systems, burns, surgical wounds, invasive medical devices or serious underlying health problems. In healthcare environments, MRSA can survive on surfaces and fabrics, including privacy curtains or garments worn by care providers. Complete surface sanitation is necessary to eliminate MRSA in areas where patients are recovering from invasive procedures. *P. aeruginosa* finds numerous reservoirs in a hospital: disinfectants, respiratory equipment, food, sinks, taps, toilets, showers and mops. Furthermore, it is constantly reintroduced into the hospital environment on fruits, plants, vegetables, as well by visitors and patients transferred from other facilities. Spread occurs from patient to patient on the hands of hospital personnel, by direct patient contact with contaminated reservoirs, and by the ingestion of contaminated foods and water. Thus, disinfectant use of a non-cytotoxic composition in these environs is expected to be highly effective and particularly advantageous in not being cytotoxic, and in some embodiments, non-irritating, to biological tissues and materials.

Devices useful in the preparation of the substantially non-cytotoxic composition are also provided. In one embodiment, particulate chlorine-dioxide-forming reactants are present in a first dispenser, such as a syringe, and a thickener component in an aqueous medium is present in a second dispenser. The aqueous thickened fluid in the second dispenser can be added directly to the particulate mixture in the first dispenser, the combination allowed to react to produce $ClO_2$, and then mixed until homogeneous. Alternatively, an aqueous medium can be added to the particulate chlorine-dioxide-forming reactants to prepare a substantially pure chlorine dioxide solution. The appropriate amount of this solution is then mixed with the aqueous thickener in the other dispenser. Both of these embodiments are advantageously practiced using syringes as the dispenser. In either embodiment, the two syringes can be connected to each other, and the contents combined by dispensing the contents of one syringe into the other, then dispensing the mixture back into the other syringe until the mixture is homogeneous. In another embodiment, the two dispensers are the two barrels of a dual barrel syringe.

In another embodiment, particulate chlorine-dioxide-forming reactants, such as ASEPTROL materials, and the aqueous medium, such as an aqueous thickened fluid, may be retained in a dispensing unit that separates the particulate reactants from the aqueous medium prior to use, and allows the two constituents to combine when dispensed. The dispensing unit can comprise a single housing unit having a separator or divider integrated with the housing so the particulate chlorine-dioxide-forming reactants and the aqueous medium only meet after being dispensed from the dispensing unit. Alternatively the dispensing unit can comprise a single housing unit having a frangible separator or divider that initially separates the particulate reagents and aqueous medium, but then permits the particulate reactants and aqueous medium to mix when the frangible divider is penetrated. Still another variation on the dispensing unit involves a dispensing unit that holds at least two individual frangible containers, one for the particulate reactants and the other for the aqueous medium; the individual frangible containers break upon the application of pressure. These and other dispensing units are fully described in U.S. Pat. No. 4,330,531 and are incorporated herein by reference in their entirety.

A kit comprising the composition, or the ingredients therefor, and an instructional material, which describes the preparation and use of the composition, is also provided. As used herein, an "instructional material," includes a publication, a recording, a diagram, or any other medium of expression which can be used to communicate the usefulness of the composition and/or compound in a kit. The instructional material of the kit may, for example, be affixed to a container that contains the compound and/or composition or be shipped together with a container which contains the compound and/or composition. Alternatively, the instructional material may be shipped separately from the container with the intention that the recipient uses the instructional material and the compound cooperatively. Delivery of the instructional material may be, for example, by physical delivery of the publication or other medium of expression communicating the usefulness of the kit, or may alternatively be achieved by electronic transmission, for example by means of a computer, such as by electronic mail, or download from a website.

In an embodiment, the kit comprises two dispensers useful for preparing the composition. One dispenser comprises a particulate precursor of chlorine dioxide. The second dispenser comprises a thickener component in an aqueous medium.

In another embodiment, the kit comprises a dispensing unit comprising a mixture of particulate chlorine-dioxide-forming reactants (particulate precursor) and an aqueous medium. In one embodiment, the dispensing unit comprises a single housing unit having a separator or divider integrated with the housing so the particulate precursor and the aqueous medium only meet after being dispensed from the dispensing unit. In another embodiment, the dispensing unit comprises a single housing unit having a frangible separator or divider that initially separates the particulate precursor and aqueous medium, but then permits the particulate precursor and aqueous medium to mix when the frangible divider is penetrated. In a third embodiment, the dispensing unit comprises a dispensing unit that holds at least two individual frangible containers, one for the particulate precursor and the other for the aqueous medium; the individual frangible containers break upon the application of pressure.

In some embodiments of the kit, the particulate precursor is ASEPTROL granules, such as ASEPTROL S-Tab2 granules. In some embodiments of the kit, the thickener component is CMC. In some embodiments of the kit, the particulate precursor comprises ASEPTROL S-Tab2 granules and the thickener component comprises CMC.

EXAMPLES

The compositions, systems, devices, and methods are further described in detail by reference to the following experimental examples. These examples are provided for purposes of illustration only, and are not intended to be limiting unless otherwise specified. Thus, the compositions, systems, devices, and methods should in no way be construed as being limited to the following examples, but rather, should be construed to encompass any and all variations which become evident as a result of the teaching provided herein.

Experimental Example 1

Cytotoxicity Analysis

To test the effects of chlorine dioxide on mammalian cells, the following experiment was performed. Two series of samples comprising different amounts of chlorite anion were prepared. Examples 1-4 used a super absorbent polyacrylate gel (labeled gel type "S"). Examples 5-8 used a carboxymethylcellulose (CMC) gel (labeled gel type "C").

ASEPTROL S-Tab2 granules were used in the gel compositions used in this experiment. The chemical composition of the granules is shown in Table 1.

TABLE 1

| Component | % (wt/wt) |
|---|---|
| Sodium chlorite | 7% |
| Dichloroisocyanuric acid, sodium salt | 1% |
| Sodium bisulfate | 12% |
| Sodium chloride | 40% |
| Magnesium chloride | 40% |

Sodium chlorite (Aragonesas Energia of Spain) was technical grade, containing nominally 80% (0.8) by weight $NaClO_2$ and 20% inorganic stabilizer salts such as NaCl, NaOH, $Na_2CO_3$, and $Na_2SO_4$. Dichloroisocyanuric acid sodium salt ($NaCl_2(CNO)_3 \cdot 2H_2O$) was obtained from Oxychem as ACL-56.

The tablets, from which granules were made, were prepared as essentially as described in Example 4 of U.S. Pat. No. 6,432,322, incorporated herein by reference. In brief, each of the separate components of the granules was dried. The appropriate quantities of the components were mixed together and the mixture was compacted into tablet form using a hydraulic table press. The thus-formed tablets were ground into granules using a mortar and pestle. The resultant granules were screened using a 40 mesh US Standard screen; the −40 mesh size fraction was used in the experiments.

ASEPTROL S-Tab2 tablets have a high degree of conversion of chlorite anions to $ClO_2$ (see Examples in U.S. Pat. No. 6,432,322). Typically, a solution made from such tables will contain about 10× as much $ClO_2$ as residual chlorite anion. When contacted with water (liquid), the water is absorbed into the pores of the tablet, where it forms a saturated aqueous solution of the constituents. Such conditions (high concentration of chlorite anion and low pH) are advantageous for the reaction of chlorite anion ($ClO_2^-$) with acid or chlorine to produce chlorine dioxide ($ClO_2$) by reactions:

$$5NaClO_2 + 4H^+ \rightarrow 4ClO_2 + NaCl + 4Na^+ + 2H_2O \quad \text{Eq. 3}$$

$$2NaClO_2 + OCl^- + H^+ \rightarrow 2ClO_2 + NaCl + NaOH \quad \text{Eq. 4}$$

Residual chlorite anion in solution can result from several sources. One source of residual chlorite anion in solution is sodium chlorite, which dissolves from the exterior surface of an ASEPTROL tablet (or granule) into the bulk solution. The conversion rate of chlorite anion to $ClO_2$ is low at the very dilute and generally neutral-pH conditions of the bulk solution, so any chlorite anion that dissolves from the exterior of a tablet or granule will remain substantially unconverted and remain as chlorite anion in solution. As a result, anything that enhances surface dissolution of sodium chlorite prior to its conversion to $ClO_2$ will result in an increase in chlorite anion concentration in the resultant solution or gel.

Each base gel (aqueous thickened fluid) was slightly different to compensate for the different active ingredient concentrations in the final samples. The final concentration of thickener component in the prepared gel samples was the same within each series. Each sample was made in an about 30 gram amount. The base gels were prepared by combining deionized water with the gelling agents (thickener component). To allow the gelling agents to become fully hydrated, the mixtures were allowed to stand for several hours to overnight. The base gel mixtures were then stirred to homogenize the base gel.

The samples were prepared by combining ASEPTROL granules with a base gel shortly before use. The exposure of the ASEPTROL material to ambient humidity or water was minimized prior to use to avoid loss of potency. After ASEPTROL granules were added to the base gel, the samples were mixed for 30 seconds with a stainless steel or plastic spatula, capped and left to stand at room temperature for 5 minutes. The samples were then mixed a second time for 30 seconds to homogenize the sample. Prepared samples were tightly capped until time of testing. The sodium chlorite granules and the prepared samples were protected from strong uv lights to limit uv-induced decomposition. Testing was begun no more than 2 hours after the samples were prepared.

Chlorine dioxide concentration was assessed by pH 7 buffered titration using potassium iodide (KI) and sodium thiosulfate on other samples. Samples 1 and 5 had zero chlorine dioxide. Samples 2 and 6 had about 30 ppm $ClO_2$. Samples 3 and 7 had about 40 ppm and samples 4 and 8 had about 580 ppm $ClO_2$.

There is not an extremely accurate method for measuring directly chlorite anions in a thickened fluid composition. Thus, the maximum concentration of chlorite anion possibly present in each prepared sample is provided below. It is expected that the actual amount of chlorite anion is less the maximum, as the reactants are activated in the presence of an aqueous medium and generate chlorine dioxide, thus consuming chlorite anions. The maximum amount of chlorite anion possibly present in a sample was calculated using the following formula:

((wt. S-Tab2 granules×wt. fraction sodium chlorite in granules×wt. fraction chlorite in sodium chlorite×nominal wt. fraction of sodium chlorite)× 1000)/total wt of final sample.

The weight fraction of sodium chlorite used in S-Tab2 granules is 0.07. The weight fraction of chlorite in sodium chlorite is 0.74. The nominal weight fraction of actual sodium chlorite in the sodium chlorite powder (i.e., the purity of the sodium chlorite) used in the granules is 0.8. Thus, for instance, the calculation of the milligrams of oxy-chlorine anion per gram of gel for sample 2 is:

((0.143 g.×0.07×0.74×0.8)×1000)/30 grams final sample.

The final formulation for the examples is shown in Tables 2 and 3.

TABLE 2

| Component | Sample 1 | Sample 2 | Sample 3 | Sample 4 |
|---|---|---|---|---|
| Sodium polyacrylate[1] | 1.4 | 1.4 | 1.4 | 1.4 |
| NaCl | 1 | 1 | 1 | 0 |
| Polyethylene oxide[2] | 1.6 | 1.6 | 1.6 | 1.6 |
| Deionized water | 26 | 25.9 | 25.6 | 25.6 |

TABLE 2-continued

| Component | Sample 1 | Sample 2 | Sample 3 | Sample 4 |
|---|---|---|---|---|
| S-Tab2 granules (−40 mesh) | 0 | 0.143 | 0.357 | 1.43 |
| Maximum mg chlorite per gram gel | 0 | 0.2 | 0.5 | 2.0 |

[1]LUQUASORB 1010, BASF Corp
[2]POLYOX WSR N3000, Dow Chemical Corp.

TABLE 3

| Component | Sample 5 | Sample 6 | Sample 7 | Sample 8 |
|---|---|---|---|---|
| Sodium carboxymethylcellulose (NaCMC)[1] | 0.75 | 0.75 | 0.73 | 0.73 |
| $Na_2HPO_4$ | 0 | 0 | 0 | 0.2 |
| Deionized water | 29.3 | 29.3 | 29.3 | 29.2 |
| S-Tab2 granules (−40 mesh) | 0 | 0.143 | 0.357 | 1.43 |
| Maximum mg chlorite per g gel | 0 | 0.2 | 0.5 | 2.0 |

[1]Sigma Aldrich 419338

Each prepared sample was tested in accordance with USP<87>. The method involves determining the biological reactivity of mammalian cell cultures following contact with a topical gel product using an agar diffusion test. The cells in this test are L929 mammalian (mouse) fibroblast cells cultured in serum-supplemented MEM (minimum essential medium). A cell monolayer of greater than 80% confluence is grown at 37° C. in a humidified incubator for not less than 24 hours and is then overlaid with agar. The agar layer serves as a "cushion" to protect the cells from mechanical damage, while allowing diffusion of leachable chemicals from the test specimen. Materials to be tested are applied to a piece of filter paper, which is then placed on the agar.

Specifically, a paper disk is dipped in sterile saline to saturate the disk. The amount of saline absorbed is determined (disk is weighed before and after wetting). A quantity of test specimen is dispensed onto the surface of the wetted disk. The specimen aliquot is kept within the boundaries of the disk but is not spread out over the entire disk. The disk with the specimen aliquot is weighed again to assess the amount of sample on the disk. The disk is then placed on top of the agar overlay. Cultures are evaluated periodically over time for evidence of cytotoxicity and are graded on a scale of 0 (no signs of cytotoxicity) to 4 (severe cytotoxicity), as summarized in Table 4. A sample is deemed to meet the requirements of the test if none of the cell culture exposed to the sample shows greater than mild cytotoxicity (grade 2) after 48 hours of testing. A sample showing grade 3 or 4 reactivity during the 48 hours is deemed cytotoxic.

TABLE 4

| Grade | Reactivity | Description of Reactivity Zone |
|---|---|---|
| 0 | None | No detectable zone around or under specimen |
| 1 | Slight | Some malformed or degenerated cells under specimen |
| 2 | Mild | Zone limited to area under specimen |
| 3 | Moderate | Zone extends to 0.5 to 1.0 cm beyond specimen |
| 4 | Severe | Zone extends greater than 1.0 cm beyond specimen |

The volume tested of each prepared example in this experimental example was about 0.1 cc (0.1 ml). The results are shown in Table 5.

TABLE 5

| Sample # | Gel Type | Maximum mg chlorite per g gel | Test result |
|---|---|---|---|
| 1 | S | 0 | Pass |
| 2 | | 0.2 | Pass |
| 3 | | 0.5 | Fail |
| 4 | | 2.0 | Fail |
| 5 | C | 0 | Pass |
| 6 | | 0.2 | Pass |
| 7 | | 0.5 | Fail |
| 8 | | 2.0 | Fail |
| Positive control | | | Fail |
| Negative control | | | Pass |

Samples 1, 2, 5, and 6 met the criteria of USP biological reactivity in vitro, indicating biocompatibility. Samples 3, 4, 7, and 8 did not meet the requirements of the USP biological test in vitro. Thus, gels having a maximum concentration of chlorite anion greater than about 0.2 mg chlorite anion/gram gel produced cytotoxic effect in this experiment.

These data suggest that cytotoxicity is related in a dose-dependent manner to the presence of chlorine dioxide, oxy-chlorine anions or some other constituent(s) of S-TAB2 granules.

Experimental Example 2

Cytotoxicity Analysis

To confirm that cytotoxicity is induced by oxy-chlorine anions and not to other possibly noxious ingredients, the following experiment was performed.

A series of samples was prepared to test various ingredients or conditions for their role in inducing cytotoxicity. ASEPTROL S-Tab10 tablets were used to prepare some of the samples in this experiment. The chemical composition of the tablets is shown in Table 6. ASEPTROL S-Tab10 tablets were prepared essentially as described in Example 5 of U.S. Pat. No. 6,432,322.

TABLE 6

| Component | % (wt/wt) |
|---|---|
| Sodium chlorite | 26% |
| Dichloroisocyanuric acid, sodium salt | 7% |
| Sodium bisulfate | 26% |
| Sodium chloride | 20% |
| Magnesium chloride | 21% |

All of the samples comprised NaCMC as the thickener component. Samples 9, 16, and 17 were prepared using −40 mesh fraction granules prepared from ASEPTROL S-Tab10 tablets. Samples 10, 19 and 20 were prepared using the ingredients of ASEPTROL S-Tab10 tablets in a non-granulated form. Specifically, the five ingredients were dried and mixed to form a powder having the composition shown in Table 5; the powder was not compacted and granulated. Thus, samples 9 and 10 have identical chemical composition but are made with the solid component in a different physical form. Similarly, samples 16 and 19 have identical compositions, as do samples 17 and 20. Samples 11-14 were prepared using a powder having a subset of the ingredients in the ASEPTROL tablets, wherein one or more ingredients was replaced (see second column of Table 7 for details). Sample 15 contained substantially pure $ClO_2$. Sample 18 was NaCMC alone.

Samples 9-14 and 16-20 were prepared as described in Experimental Example 1. In brief, the samples were prepared by combining the solid fraction (e.g., ASEPTROL granules) with a base gel shortly before use. The base gel was NaCMC that was allowed to hydrate. After the solid fraction was added to the base gel, the samples were mixed for 30 seconds with a stainless steel or plastic spatula, capped, and left to stand at room temperature for 5 minutes. The samples were then mixed a second time for 30 seconds to homogenize the sample. Prepared samples were tightly capped until time of testing. The sodium chlorite granules and other solid mixture comprising sodium chlorite, and the prepared samples were protected from strong uv lights to limit uv-induced decomposition. Testing was begun no more than 2 hours after the samples were prepared.

Sample 15 was prepared using a base gel of hydrated NaCMC and a substantially pure chlorine dioxide solution that was prepared on the same day the sample was prepared and the test begun. The base gel was prepared by adding 0.75 gm of sodium carboxymethylcellulose powder (Sigma-Aldrich, 700,000 mole. wt., typ.) to 19.2 gm of deionized water, allowing the mixture to stand in a covered jar for overnight, and mixing to homogenize the base gel. The substantially pure chlorine dioxide solution was prepared as follows: Twelve (12) ASEPTROL S-Tab10 tablets (1.5 grams each) were placed into 1 liter of potable tap water, producing a deep yellow colored source solution of >1000 ppm chlorine dioxide. Air was bubbled into the bottom of the source solution at a rate of about 1 liter per minute to strip chlorine dioxide from the source solution into the air. The resultant chlorine dioxide-laden air was then bubbled into the bottom of 1 liter of deionized water to form a solution of pure chlorine dioxide. Only $ClO_2$ and possibly some water vapor was transferred from the source to the product solution. All the salt ingredients remained behind in the source solution. As a result, the product solution was a substantially pure solution of $ClO_2$. Bubbling was ended when the yellow color of the source solution was nearly gone. A sample of the substantially pure chlorine dioxide solution was analyzed for chlorine dioxide concentration using a Hach Model 2010 UV/Visible spectrophotometer; the substantially pure solution was found to contain 700 ppm chlorine dioxide by weight. Ten (10) grams of the 700 ppm pure chlorine dioxide solution was added to the base gel and mixed to produce a gel containing about 233 ppm chlorine dioxide and substantially no oxy-chlorine anions. As above, the $NaClO_2$-containing components and the prepared samples were protected from strong uv lights to limit uv-induced decomposition. All dry solid ingredients were protected from water exposure (e.g., ambient humidity) as well.

The samples were tested as described in Experimental Example 1, except samples 17 and 20 were tested at an 0.04 cc dose, rather than an 0.1 cc dose. Testing was begun no more than 2 hours after the samples were prepared.

The results are shown in Table 7.

TABLE 7

| Sample # | | Maximum mg chlorite per gram final gel | Result of USP <87> |
|---|---|---|---|
| 9 | Prepared with ASEPTROL S-Tab10 granules | 0.5 | Fail |
| 10 | Prepared with non-granulated ingredients of ASEPTROL S-Tab 10 | 0.5 | Fail |
| 11 | NaDCCA replaced with cyanuric acid | 0.5 | Fail |

TABLE 7-continued

| Sample # | | Maximum mg chlorite per gram final gel | Result of USP <87> |
|---|---|---|---|
| 12 | $NaClO_2$ replaced with NaCl | 0 | Pass |
| 13 | NaDCCA removed | 0.5 | Fail |
| 14 | $NaClO_2$ replaced with NaCl, and NaDCCA replaced with cyanuric acid | 0 | Pass |
| 15 | Prepared with pure $ClO_2$ (no other salts) | 0 | Pass |
| 16 | Sample 9 prepared with 3x the water | 0.17 | Fail |
| 17 | Sample 9, 0.04 cc dose on disk | 0.5 | Fail |
| 18 | NaCMC alone with no granules, salts or $ClO_2$ | 0 | Pass |
| 19 | Sample 10 prepared with 3x the water | 0.17 | Fail |
| 20 | Sample 10, 0.04 cc dose on disk | 0.5 | Fail |
| | Positive control | 0 | Fail |
| | Negative control | 0 | Pass |

Samples 9-11, 13, 16, 17, 19, and 20 all failed to meet the criteria for USP biological reactivity in vitro. Thus, mimicking the elution-type test of USP<87> did not alter the results (compare samples 10 and 19, and samples 9 and 16). Reducing the dose did not alter the results (compare sample 9 and 17, and samples 10 and 20). These data indicate that neither the dose used in the test nor the use of gel with 3× the water play a role in the observed cytotoxicity.

The results for samples 9 and 10 indicate that the physical form of the ASEPTROL component does not noticeably affect the cytotoxicity. The results for samples 11 and 13 indicate that the presence of a chlorine-producing agent, NaDCCA, does not noticeably affect the cytotoxicity. This result suggest that the observed cytotoxicity does not result from chlorine.

Samples 12, 14, 15, and 18 met the criteria for USP biological reactivity in vitro, indicating biocompatibility. These data indicate that the cytotoxicity is not caused by the gellent alone (Sample 18). The observation that Sample 15, which contained pure $ClO_2$ and no other salts, did not cause cytopathic effect indicates that chlorine dioxide itself is not the cause of cytotoxicity observed in the samples comprising ASEPTROL S-Tab10 granules.

The common feature of samples 12, 14, 15, and 18 is that none contain chlorite anion. Thus, none of samples 12, 14, and 18 contains oxy-chlorine anions. It is formally possible that sample 15, comprising pure $ClO_2$, may contain some oxy-chlorine anions due to the decomposition of $ClO_2$, however, the amount is insignificant.

In view of these results, it is concluded that oxy-chlorine anions are the causative agent underlying the cytotoxicity observed in these experiments.

Experimental Example 3

Cytotoxicity Analysis

The data in Experimental Example 1 indicate that the cytotoxicity of oxy-chlorine anions is dose dependent. Specifically, cytotoxicity was not observed in gels having a maximum of 0.2 mg chlorite anion per gram gel, whereas cytotoxicity was observed in gels having a maximum of 0.5 mg chlorite anion/gram. This experiment was designed to further examine the cytotoxicity of chlorite anions, using sodium chlorite solution, which permits an more accurate estimate of chlorite anion concentration in the thickened fluid compositions tested. In addition, the cytotoxicity of a commercially-available over-the-counter, peroxide-based, tooth whitening product, containing 10% hydrogen peroxide as the bleaching agent was also assessed.

Sample 22-24 were prepared by combining an aqueous solution of sodium chlorite with a base gel shortly before use. Thus, none of samples 22-25 contained chlorine dioxide. These samples also did not contain an acid source or a free halogen source. Samples 22-24 were prepared by mixing the aqueous sodium chlorite solution with the base gel for 30 seconds, capping the sample and letting it stand at room temperature for 5 minutes, the mixing for another 30 seconds. Sample 25 was similarly prepared but using water instead of a sodium chlorite solution. None of samples 22-25 contained an acid source or a free halogen source.

Sample 26 is an over-the-counter (OTC) product that is a gel containing 10% hydrogen peroxide; the gel material was used as present on the foil-wrapped strip.

Sample 21 was prepared using a substantially pure chlorine dioxide solution prepared by reacting ASEPTROL S-Tab10 tablets into water. Specifically, one 1.5 mg tablet was reacted in 200 ml $H_2O$. The resulting chlorine dioxide solution was not sparged. Chlorine dioxide concentration of the solution was about 733 ppm, as assessed using a Hach Model 2010 uv-vis spectrophotometer. Sample 21 thus had about 244 ppm $ClO_2$, after dilution of 1 part solution with 2 parts of gel The cytotoxicity results are shown in Table 8.

TABLE 8

| Sample # | Gel | Mg chlorite per gel | Result of USP <87> |
|---|---|---|---|
| 21 | CMC | 0 (Made with ~700 ppm $ClO_2$ solution) | Pass |
| 22 | | 0.04 | Pass |
| 23 | | 1.0 | Fail |
| 24 | | 2.0 | Fail |
| 25 | | 0 | Pass |
| 26 | unknown | OTC product with 10% hydrogen peroxide | Fail |
| | | Positive control | Fail |
| | | Negative control | Pass |

The results for Samples 22-24 indicate that chlorite anion at elevated concentration is cytotoxic to human cells, confirming the conclusions from Experimental Example 2. The result for Sample 21 indicates that a high chlorine dioxide concentration thickened fluid composition that is non-cytotoxic can be prepared using substantially pure chlorine dioxide solution prepared using ASEPTROL S-Tab10 tablets.

This data also shows that 10% $H_2O_2$ is cytotoxic (Sample 26) to mammalian cells. Indeed, the reactivity zone extended more than 1 cm beyond the gel specimen, suggesting severe cytotoxicity.

Experimental Example 4

Additional Cytotoxicity Studies

To further examine the relationship between cytotoxicity and oxy-chlorine anion concentration in a thickened fluid composition, the following experiment was performed.

Samples 27-31 were prepared by combining an aqueous solution of sodium chlorite (10 ml) with 20 g of a base gel (hydrated high viscosity NaCMC) shortly before use. The NaCMC was a USP grade CMC, obtained from Spectrum Chemical (stock # CA194); a 1% aqueous solution has a viscosity of about 1500-3000 cp. The base gel was prepared using 0.85 g. of NaCMC per 30 g final composition in order to achieve rheology equivalent to that for the CMC obtained from Sigma Aldrich. None of samples 27-30 contained chlorine dioxide. Sample 27 was similarly prepared but using water instead of a sodium chlorite solution. Samples 26-30 were prepared by mixing the aqueous sodium chlorite solution (or water) with the base gel until homogenous.

Sample 31, having the same relative composition as Sample 6 and about 40 ppm chlorine dioxide, was prepared using a two-syringe mixing method. One syringe contained –40 mesh ASEPTROL S-Tab2 granules (0.048 g). The second syringe contained the base gel (10 grams). The contents of the two syringes were combined as follows. The syringe containing the granules was held with the tip pointing up. The outlet plug was removed and a nylon connector was attached. The other end of the nylon connector was attached to the outlet of the syringe containing the base gel. The plunger of the gel syringe was slowly depressed, expelling the gel into the granules. The gel-and-granules mixture was then allowed to sit for 5 minutes to activate the granules thereby generating chlorine dioxide; the syringes remained connected during this period. After 5 minutes, the syringe plungers were alternately depressed at a brisk rate to move the mixture back and forth between the two syringe bodies at least 15 times, or until the sample was homogenous in color. The gel was then ready for use the agar diffusion test of USP<87>.

The results of the cytotoxicity testing are shown in Table 9.

TABLE 9

| Sample # | Gel | Mg chlorite per gel | Result of USP <87> |
|---|---|---|---|
| 27 | CMC | 0 | Pass |
| 28 | | 0.1 | Pass |
| 29 | | 0.2 | Fail |
| 30 | | 0.4 | Fail |
| 31 | | 0.2* | Pass |
| | | Positive control | Fail |
| | | Negative control | Pass |

*maximum amount of chlorite anion possibly present; calculated as described in Experimental Example 1

These data further support the discovery that chlorite anion is cytotoxic to human cells in a dose-dependent relationship. Sample 29, which contains 0.2 mg chlorite per gram final composition, failed the test, whereas Sample 28, which contains 0.1 mg chlorite anion per gr did not fail. This suggests that chlorine dioxide compositions having less than 0.2 mg chlorite anion per gram composition are not cytotoxic to human cells. This outcome also supports the expectation that chlorite anions present in gels made with ASEPTROL granules or powders is consumed in the generation of chlorine dioxide. Specifically, gels prepared using ASEPTROL granules or powder and having a maximum possible amount of 0.2 mg chlorite anion per gram final composition were found to be non-cytotoxic. Thus, the apparent concentration of chlorite anions in these gels is estimated to be less than 0.2 mg chlorite per gram.

Experimental Example 5

Antimicrobial Studies

An experiment was performed to ascertain the antimicrobial efficacy of non-cytotoxic chlorine dioxide solutions and thickened compositions. Non-cytotoxic chlorine dioxide solutions are three different chlorine dioxide concentrations were tested. Non-cytotoxic chlorine dioxide thickened compositions prepared in different ways, were tested.

Two opportunistic pathogens of humans were used in the studies: methicillin-resistant *Staphylococcus aureus* (MRSA) and *Pseudomonas aeruginosa* (*P. Aeruginosa*).

Samples 32-34 are chlorine dioxide solutions containing ~599 ppm, ~99 ppm and ~40 ppm chlorine dioxide, respectively. Samples 35 and 36 are thickened chlorine dioxide compositions containing ~110 ppm chlorine dioxide and ~40 ppm chlorine dioxide, respectively.

Samples 32-34 were prepared as follows. A substantially pure chlorine dioxide solution comprising 599 ppm chlorine dioxide was made by adding two 1.5 gram S-Tab10 tablets into 400 ml of deionized water in a 16 oz amber jar. The jar was capped and the tablets allowed to react with the water without stirring or agitation for 10 minutes at room temperature. The jar was then swirled to mix the contents and to dissolve any remaining solids. The chlorine dioxide concentration in the final solution was measured using a Hach 2010 spectrophotometer. Three additional solutions (~319 ppm, ~99 ppm and ~40 ppm) were made by appropriate dilution, with deionized water, of the 599 ppm chlorine dioxide solution.

Samples 35 and 36 were prepared using a first and second base gel. The first and second base gels were slightly different; however the final concentration of thickener component in the prepared gel samples 35 and 36 was the same. Each sample was made in an about 30 gram amount. The base gels were prepared by combining deionized water with the gelling agents (thickener component). To allow the gelling agents to become fully hydrated, the mixtures were allowed to stand for several hours to overnight. The base gel mixtures were then stirred to homogenize the base gel.

Sample 35 was prepared by combining 10 ml of ~319 ppm chlorine dioxide solution (preparation described above with regard to samples 32-34) with 20 grams of a first base gel shortly before use. After the solution was added to the base gel, the sample was mixed for 30 seconds with a stainless steel or plastic spatula, capped and left to stand at room temperature for 10 minutes. The samples were then mixed a second time for 30 seconds to homogenize the sample.

Sample 36 was prepared by combining the solid fraction (~40 mesh ASEPTROL S-Tab2 granules) with 30 grams of a second base gel shortly before use. The base gel was NaCMC that was allowed to hydrate. After the solid fraction was added to the base gel, the samples were mixed for 30 seconds with a stainless steel or plastic spatula, capped and left to stand at room temperature for 5 minutes. The samples were then mixed a second time for 30 seconds to homogenize the sample.

The prepared samples were tightly capped until time of testing. The ASEPTROL granules, and the prepared samples were protected from strong uv lights to limit uv-induced decomposition.

Testing was begun no more than 2 hours after the samples were prepared.

Efficacy of the samples against the two pathogens, MRSA ATCC 33591 and *P. aeruginosa* ATCC 9027, was assessed using the Dow 923 "Shake Flask" Test in accordance with USP 29, chapter 61, Microbiological Examination of Nonsterile Products: Microbial Enumeration Tests (@2007). In brief, initial dilutions were made in Brain-Heart infusion broth. The final dilution was made in 75 ml phosphate buffered water. A standard plate count was performed on each shake flask to determine the initial organism population. The test article amount (0.75 g) was weighed and placed into separate sterile disposable PBW containers with the inoculated 75 ml phosphate-buffered water. Sample inoculum levels were 420,000 cfu/ml and 250,000 cfu/ml for MRSA and *P. aeruginosa*, respectively. Each flask was placed into a wrist action shaker and vigorously shaken for one (1) hour. Flasks were removed from the shaker, and the test solution was placed in Petri dishes. Standard Methods agar was then added, and the dishes incubated. Aerobic plate count/ml was assessed at 15 minute, 30 minutes, 1 hour and 24 hours.

The results are summarized in Table 10.

TABLE 10

| Sample | $ClO_2$ (ppm) | Pathogen | Number of surviving organisms after incubation time: 15 min, 30 min, 1 hr and 24 hr |
|---|---|---|---|
| 32 | 599 | MRSA | <1 per ml* at all incubation times |
|  |  | *P. aeruginosa* | <1 per ml* at all incubation times |
| 33 | 99 | MRSA | <1 per ml* at all incubation times |
|  |  | *P. aeruginosa* | <1 per ml* at all incubation times |
| 34 | 40 | MRSA | <1 per ml* at all incubation times |
|  |  | *P. aeruginosa* | <1 per ml* at all incubation times |
| 35 | 106 | MRSA | <1 per ml* at all incubation times |
|  |  | *P. aeruginosa* | <1 per ml* at all incubation times |
| 36 | 40 | MRSA | <1 per ml* at all incubation times |
|  |  | *P. aeruginosa* | <1 per ml* at all incubation times |

*limit of detection for the method used.

The data demonstrate that at all concentrations of chlorine dioxide, whether in solution or a gel (thickened fluid composition), the substantially non-cytotoxic compositions exhibited potent antimicrobial activity against both MRSA and *P. aeruginosa*. Thus, the antimicrobial activity of chlorine dioxide-containing compositions does not require the oxy-chlorine anion that is cytotoxic. Substantially non-cytotoxic compositions are therefore useful as disinfectant reagents for hard surfaces and for treating against bacteria in wounds.

Experimental Example 6

Wound Healing Studies

To determine if a non-cytotoxic chlorine dioxide thickened composition in topical administration adversely affects wound healing, the following experiment was performed using pigs as the animal model. Pigs are frequent models for wound healing in part because pig skin shares many characteristics with human skin. The porcine model is considered to be an excellent tool for the evaluation of candidate agents intended for use in human wounds.

The experiment used three female Yorkshire swine, each weighing between 45 to 52 lb at the start of the experiment. The pigs were housed in accordance with "Guide for the Care and Use of Laboratory Animals DHEW" (NIH). They were fed fresh porcine diet daily and water was available ad libitum. The pigs were housed in a temperature-controlled animal room, having a 12-hour light/dark cycle. The room was kept clean and free of vermin.

Animals were anesthetized with isoflurane and eight (8) full-thickness excisions (2.5 cm×2.5 cm square) were made on each anima, four per flank. Thus, there were a total of 24 separate test sites. Three different samples, 37-39, were tested, each at 6 sites. The remaining 6 sites served as non-treated control. A 0.5 ml aliquot of a sample was applied to a test site daily for 7 consecutive days.

Samples 37 and 38 are thickened aqueous fluid compositions comprising chlorine dioxide at about 40 ppm and about 200 ppm, respectively. The base gel for sample 37 was slightly different from the base gel for sample 38, however the final concentration of thickener component in the prepared gel samples 37 and 38 was the same. Each sample was made in an about 30 gram amount. The base gels were prepared by combining deionized water with the gelling agents (thickener component). To allow the gelling agents to become fully hydrated, the mixtures were allowed to stand for several hours to overnight. The base gel mixtures were then stirred to homogenize the base gel.

Sample 37 was prepared in the same manner Sample 36 was prepared. Sample 38 was prepared in the same manner as Sample 35, with the difference being a 10 ml aliquot of an about 600 ppm chlorine dioxide solution (prepared as described in Experimental Example 5) was used, yielding about 30 grams of an about 200 ppm chlorine dioxide aqueous gel.

Sample 39 is an about 200 ppm aqueous solution of chlorine dioxide. Sample 39 was prepared by diluting an about 600 ppm substantially pure chlorine dioxide solution (prepared as described in Experimental Example 5) with deionized water.

The prepared samples were tightly capped until time of testing. The sodium chlorite granules, and the prepared samples were protected from strong uv lights to limit uv-induced decomposition. Testing was begun no more than 2 hours after the samples were prepared. Samples were prepared fresh each day.

The effect of each sample on wound healing was assessed by assessing wound area contraction. Each wound area was traced on clear acetate on Day 0 and Day 7 of the study for wound area determinations. The tracings of the wounds were cut out of the acetate sheet and weighed. A conversion factor (grams to square centimeters) was generated by weighing a 10 cm×10 cm section of the same acetate sheet. Wounds were photographed at termination on Day 7. Wound area contraction is calculated using the following formulation: (Day 1 area−Day 7 area)/Day 1 area.

Each sample was applied daily for seven consecutive days. The wounds were dressed daily with polyurethane film dressings and secured with ELASTIKON tape (Johnson & Johnson, New Brunswick N.J.).

TABLE 11

| Sample | Brief description | % Wound contraction (n = 6) | SEM |
| --- | --- | --- | --- |
| 37 | 40 ppm aqueous gel | 55.84 | 3.86 |
| 38 | 200 ppm aqueous gel | 56.92 | 3.0 |
| 39 | 200 ppm aqueous solution | 50.10 | 3.16 |
| n/a | Non-treated wounds (Control) | 57.49 | 2.94 |

The data are shown in Table 11. There was no statistical difference in the full-thickness contraction rates of the treated wounds compared to the control wounds. Thus, it is concluded that topical administration of non-cytotoxic chlorine dioxide thickened compositions to full-thickness dermal wounds does not adversely affect the rate of wound healing.

The disclosures of each and every patent, patent application, and publication cited herein are hereby incorporated herein by reference in their entirety.

While the compositions, systems, devices, and methods have been disclosed with reference to specific embodiments, it is apparent that other embodiments and variations may be devised by others skilled in the art without departing from the true spirit and scope of the compositions, systems, devices, and methods. The appended claims are intended to be construed to include all such embodiments and equivalent variations.

What is claimed is:

1. A thickened fluid composition comprising:
   a) at least about 20 ppm chlorine dioxide;
   b) oxy-chlorine anions;
   c) a thickener component; and
   d) an aqueous fluid,
   wherein the composition comprises no more than about 0.25 milligrams oxy-chlorine anion per gram composition and is substantially non-cytotoxic, and wherein the thickener component is selected from the group consisting of a natural hydrocolloid, a semisynthetic hydrocolloid, a clay, a high molecular weight polyethylene glycol, a high molecular weight polypropylene glycol, a polyethylene oxide, and a carbomer.

2. The composition of claim 1, wherein the composition comprises less than about 0.2 milligrams oxy-chlorine anion per gram composition.

3. The composition of claim 2, wherein the composition comprises about 20 to about 2000 ppm chlorine dioxide.

4. The composition of claim 3, wherein the composition has a pH from about 4.5 to about 11.

5. The composition of claim 2, wherein the thickener component is selected from the group consisting of a natural hydrocolloid, a semisynthetic hydrocolloid and a clay.

6. The composition of claim 1, further comprising one or more components selected from an antibacterial agent and a malodor controlling agent.

7. The composition of claim 6, wherein the antibacterial agent is one of silver and a quaternary ammonium compound.

8. A method of making a substantially non-cytotoxic thickened fluid composition comprising chlorine dioxide, the method comprising the step of combining a chlorine dioxide solution comprising oxy-chlorine anions with a thickener component to form a substantially non-cytotoxic thickened fluid composition,
   wherein the composition comprises at least about 20 ppm chlorine dioxide and no more than about 0.25 milligrams oxy-chlorine anion per gram composition, and wherein the thickener component is selected from the group consisting of a natural hydrocolloid, a semisynthetic hydrocolloid, a clay, a high molecular weight polyethylene glycol, a high molecular weight polypropylene glycol, a polyethylene oxide, and a carbomer.

9. The method of claim 8, further comprising the step of preparing the chlorine dioxide solution comprising oxy-chlorine anions.

10. The method of claim 9, wherein the step of preparing the chlorine dioxide solution comprises dissolving a solid body in water, wherein the solid body comprises a metal chlorite, an acid source and a optional source of free halogen.

11. The method of claim 8, wherein the substantially non-cytotoxic thickened fluid composition comprises less than about 0.2 milligrams oxy-chlorine anion per gram composition.

12. The method of claim 8, wherein the substantially non-cytotoxic thickened fluid composition comprises about 20 to about 2000 ppm chlorine dioxide.

13. The method of claim 8, wherein the substantially non-cytotoxic thickened fluid composition has a pH from about 4.5 to about 11.

14. The method of claim 8, wherein the thickener component is selected from the group consisting of a natural hydrocolloid, a semisynthetic hydrocolloid and a clay.

15. The composition of claim 1, wherein the thickener component is carboxymethylcellulose.

* * * * *